United States Patent
Vogt et al.

(10) Patent No.: US 11,806,482 B2
(45) Date of Patent: *Nov. 7, 2023

(54) PLACEHOLDER SUITABLE FOR MEDICAL USE

(71) Applicant: Heraeus Medical GmbH, Wehrheim (DE)

(72) Inventors: Sebastian Vogt, Wehrheim (DE); Thomas Kluge, Wehrheim (DE); Hubert Büchner, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 611 days.

This patent is subject to a terminal disclaimer.

(21) Appl. No.: 16/879,240

(22) Filed: May 20, 2020

(65) Prior Publication Data

US 2020/0391007 A1 Dec. 17, 2020

(30) Foreign Application Priority Data

Jun. 12, 2019 (DE) .................... 102019115932.6

(51) Int. Cl.
*A61M 25/00* (2006.01)
*A61M 39/22* (2006.01)
(Continued)

(52) U.S. Cl.
CPC ...... *A61M 25/0045* (2013.01); *A61M 39/225* (2013.01); *A61M 39/24* (2013.01);
(Continued)

(58) Field of Classification Search
CPC ........ A61M 2039/0018; A61M 39/225; A61M 2039/242; A61M 2205/7536
See application file for complete search history.

(56) References Cited

U.S. PATENT DOCUMENTS 4,016,864 A * 4/1977 Sielaff ................ A61B 5/14542
422/68.1
4,188,360 A * 2/1980 Kurata .................... A61M 1/32
422/46

(Continued)

FOREIGN PATENT DOCUMENTS

JP 2002-505592 2/2002
WO 98/20939 5/1998
(Continued)

OTHER PUBLICATIONS

English Translation of Notice of Reasons for Rejection dated Jun. 29, 2021 for counterpart Japanese Patent Application No. 2020-099461.

(Continued)

*Primary Examiner* — Jenna Zhang
(74) *Attorney, Agent, or Firm* — Dicke, Billig & Czaja, PLLC

(57) ABSTRACT

A medical placeholder. The medical placeholder has at least one hollow body which is expandable and which defines an interior space, a gas infeed hose which is connected or connectable in a gas-permeable manner with the interior space of the hollow body, and a gas discharge hose which is connected or connectable in a gas-permeable manner with the interior space of the hollow body. The hollow body consists partly or completely of at least one plastic material which is permeable to oxygen and carbon dioxide. A one-way valve is arranged in the gas infeed hose and a pressure relief valve is arranged in the gas discharge hose. Also disclosed is a method for gas-flushing a surface of a medical placeholder.

18 Claims, 19 Drawing Sheets

(51) Int. Cl.
*A61M 39/24* (2006.01)
*A61M 39/00* (2006.01)

(52) U.S. Cl.
CPC ........... *A61M 2025/0056* (2013.01); *A61M 2039/0018* (2013.01); *A61M 2039/242* (2013.01); *A61M 2202/0208* (2013.01); *A61M 2202/0225* (2013.01); *A61M 2202/04* (2013.01); *A61M 2205/0205* (2013.01); *A61M 2205/7518* (2013.01); *A61M 2205/7536* (2013.01); *A61M 2210/02* (2013.01)

(56) References Cited

U.S. PATENT DOCUMENTS

| | | | |
|---|---|---|---|
| 4,576,590 | A | 3/1986 | Fiddian-Green |
| 5,122,113 | A | 6/1992 | Hattler |
| 5,219,326 | A | 6/1993 | Hattler |
| 5,376,069 | A | 12/1994 | Hattler |
| 2001/0004710 | A1 | 6/2001 | Felt et al. |
| 2007/0055276 | A1 | 3/2007 | Edidin |
| 2010/0114011 | A1* | 5/2010 | Herrmann ........... A61M 13/003 137/100 |
| 2010/0272606 | A1* | 10/2010 | Carpenter ........... A61M 60/38 422/46 |
| 2011/0196499 | A1 | 8/2011 | Boucher et al. |
| 2012/0234332 | A1* | 9/2012 | Shantha ........... A61N 1/3601 128/848 |
| 2016/0106481 | A1 | 4/2016 | Taha et al. |
| 2016/0235902 | A1* | 8/2016 | Flanagan ........... A61M 1/1698 |
| 2018/0272113 | A1 | 9/2018 | Brister et al. |

FOREIGN PATENT DOCUMENTS

| | | |
|---|---|---|
| WO | 2009/084109 | 7/2009 |
| WO | 2010/068467 A1 | 6/2010 |

OTHER PUBLICATIONS

Matsunaga, Katsuji et al., "Gas Permeability of Thermoplastic Polyurethane Elastomers" Polymer Journal, vol. 37, No. 6, pp. 413-417 (2005).

* cited by examiner

PLACEHOLDER SUITABLE FOR MEDICAL USE

CROSS-REFERENCE TO RELATED APPLICATIONS

This application claims priority under 35 U.S.C. § 119(a) to German (DE) Patent Application No. 10 2019 115 932.6, filed on Jun. 12, 2019.

TECHNICAL FIELD

The invention relates to a medical placeholder for treating bone defects. The invention also relates to a method for gas-flushing a surface of a medical placeholder. The subject matter of the invention is an expandable medical placeholder for temporary implantation into bone cavities. In addition to its place-holding function, the medical placeholder is also intended for gas exchange with the surrounding tissue, wherein oxygen or an oxygen-containing flushing gas mixture or an oxygen-enriched flushing liquid flows through an interior space of the spacer continuously or discontinuously and oxygen may be fed via the permeable outer wall of the placeholder to the tissue and carbon dioxide may simultaneously be removed.

BACKGROUND OF THE DISCLOSURE

A catheter with an oxygen-permeable tube wall which is provided for treating internal organs is known from U.S. Pat. No. 4,576,590. The material of the tube used should ideally not expand, since this could impair the internal organs. Accordingly, the device is not usable as a variable placeholder for bone defects. U.S. Patent Application Publication No. 2016/0235902 discloses a gas exchange system for a body lumen (the trachea), in which gas exchange may occur between the trachea and a membrane of the gas exchange system. This system is also not usable to treat bone defects.

Larger segmental defects in tubular bones continue to present a serious challenge for surgeons. Segmental defects may be caused inter alia by trauma, by infected pseudoarthrosis and by chronic osteitis. These bone defects are often treated using the Illizarov method. For treating major dia- and metaphyseal bone defects, with a defect size of >3 cm, the Masquelet technique is another treatment option. This technique involves a first operation in which the bone defect is extensively debrided and a bone cement spacer is inserted into the medullary cavity as a placeholder. The bone cement spacer is covered with soft tissue. Sufficient partial coverage of soft tissue is absolutely essential for treatment success. Mechanical stabilization of the bone defect is achieved by external fixation. Over a period of four to six weeks, a vascularized connective tissue membrane forms around the bone cement spacer. The periosteum is thus reconstructed. The bone cement spacer is then removed in a second operation, for which at least one lengthwise incision is usually made. In the process, it is attempted to protect the connective tissue membrane formed as much as possible, but this is difficult since the bone cement spacer has a diameter equal to the diameter of the medullary cavity. The medullary cavity is then filled with autologous cancellous bone, bone substitute materials or mixtures of autologous cancellous bone and bone substitute materials. In most cases, membrane-guided ossification then takes place along the connective tissue membrane.

It is thus disadvantageous if the connective tissue membrane is damaged on removal of the bone cement spacer or of the placeholder, since it is needed thereafter for ossification. It would furthermore be desirable for the connective tissue membrane to be constructed rapidly and robustly, in order to assist the subsequent healing process. At the same time, the placeholder should be variably adaptable to different treatment situations.

An object of the invention is to develop a medical spacer which can be implanted into bone cavities or bone defects as a temporary implant. The volume and shape of the spacer should be as variable as possible. It should be possible to remove the spacer from the bone cavities or bone defects in such a way that only minimal damage occurs to the adjacent tissue. The connective tissue membrane surrounding the spacer should be kept as intact as possible. The spacer also needs to enable gas exchange with the human tissue which adjoins the spacer directly after implantation or forms there during the implantation period. The tissue needs to be capable of being supplied with oxygen and, at the same time, the carbon dioxide arising during tissue metabolism needs to be continuously or discontinuously removed. The spacer should be suitable for use as a temporary implant in the Masquelet technique for the purpose of treating major bone defects.

SUMMARY OF THE DISCLOSURE

The objects of the invention are achieved by a medical placeholder having at least one hollow body, which is expandable and which defines an interior space in the interior of the hollow body, a gas infeed hose, which is connected or connectable in a gas-permeable manner with the interior space of the hollow body, a gas discharge hose, which is connected or connectable in a gas-permeable manner with the interior space of the hollow body, wherein the hollow body consists at least in areas or completely of at least one plastic material, which is permeable to oxygen and carbon dioxide and wherein a one-way valve is arranged in the gas infeed hose and a pressure relief valve is arranged in the gas discharge hose.

Preferably, the medical placeholder is suitable for temporary implantation into bone cavities.

Also preferably, the hollow body is made from an oxygen- and carbon dioxide-permeable plastic material.

Moreover, the hollow body is at least sufficiently expandable for the volume of the hollow body to be able to increase by at least 50%, preferably to be able to increase by at least 100%, particularly preferably to be able to increase by at least 200%.

Furthermore, the hollow body is at least sufficiently elastically expandable for the volume of the hollow body to be able to increase reversibly and non-destructively by at least 50%, preferably to be able to increase by at least 100%, particularly preferably to be able to increase by at least 200%.

Furthermore, the interior space is closed off from the surroundings of the medical placeholder.

According to a preferred further development, the at least one plastic material is impermeable to liquids.

The hollow body or the plastic hollow body forms with the gas infeed hose and the gas discharge hose a common interior space preferably closed off relative to the surroundings, such that, on infeed of pressurized flushing gas (or a flushing gas mixture) or of an oxygen-containing flushing liquid, the hollow body is able to expand. It is advantageous, to this end, for the wall of the hollow body to be formed of a rubber-elastic plastic material or a plastically deformable plastic material, such that the hollow body can be inflated or expanded. It is thus possible to adapt the shape of the hollow body and thus of the medical placeholder to the shape of the bone defect to be temporarily filled or of the cavity to be temporarily filled.

The at least one plastic material preferably forms, at least in areas, a continuous wall of the hollow body. That means that there are regions of the wall of the hollow body which consist of no other additional material apart from the at least one plastic material. Readily permeable meshes and wires, in particular of metal, are unproblematic in this respect. The intention is in this case to ensure that the permeability of the plastic material to oxygen and carbon dioxide can be used to ensure that the wall of the hollow body is likewise permeable to oxygen and carbon dioxide at least in these regions.

Thus, preferably a wall defining the interior space of the hollow body is permeable to oxygen and carbon dioxide.

According to a preferred embodiment of the present invention, the hollow body is of a tubular configuration, wherein the gas infeed hose and the gas discharge hose are preferably connected at one end face of the hollow body with the interior space of the hollow body or are connected at two mutually opposing end faces of the hollow body with the interior space of the hollow body. Tubular hollow bodies are particularly well suited to use as spacers in particular for bone defects of the long tubular bones.

The hollow body may also have any other desired shape, depending on the size and shape of the bone defect to be temporarily filled.

In the present invention, the hollow body or the at least one plastic material of the hollow body has a permeability coefficient for oxygen of greater than or equal to 0.5 $cm^3/(m^2*d*bar)$ and a permeability coefficient for carbon dioxide of greater than or equal to 0.5 $cm^3/(m^2*d*bar)$, and preferably has a permeability coefficient for oxygen of greater than or equal to 1 $cm^3/(m^2*d*bar)$ and a permeability coefficient for carbon dioxide of greater than or equal to 1 $cm^3/(m^2*d*bar)$. The unit d denotes a day.

In this way, the connective tissue membrane may be well supplied with oxygen and carbon dioxide may be readily transported away from the connective tissue membrane and in the process from the inside of the connective tissue membrane.

The permeability coefficient is determined pursuant to DIN 53380-4 (11/2006). This relates in particular to testing plastic material, in this case to the determination of gas permeability, wherein Part 4 of DIN 53380 standardizes a carbon dioxide-specific infrared absorption method for measurement of plastic films and plastic moldings which may also be applied to oxygen. Such measurements are performed and offered for sale for example by Mecadi GmbH (Bexbach, Germany).

The hollow body or the at least one plastic material of the hollow body also has a permeability coefficient for oxygen of greater than or equal to 0.5 $cm^3/(m^2*d*bar)$ and a permeability coefficient for carbon dioxide of greater than or equal to 0.5 $cm^3/(m^2*d*bar)$ to DIN 53380-4 (11/2006), and preferably has a permeability coefficient for oxygen of greater than or equal to 1 $cm^3/(m^2*d*bar)$ and a permeability coefficient for carbon dioxide of greater than or equal to 1 $cm^3/(m^2*d*bar)$ pursuant to DIN 53380-4 (11/2006).

In solids, permeability generally denotes the property of allowing gases and/or liquids to pass therethrough. In the present case, this relates to the permeability of the walls of the hollow body specifically in relation to molecular oxygen and molecular carbon dioxide in gaseous form. The permeability coefficient is a material-specific constant and is a measure of permeability for liquids and gases.

Moreover, an inflow opening of the gas infeed hose, by which the gas infeed hose opens into the interior space, is arranged spatially separately from an outflow opening of the gas discharge hose, wherein the outflow opening forms the point where the interior space opens into the gas discharge hose.

In this way, sufficiently long contact between the through-flowing flushing gas or the through-flowing flushing liquid and the internal wall of the hollow body or of the at least one plastic material is achieved during the flow through the hollow body, thereby promoting gas exchange of oxygen and carbon dioxide through the wall of the hollow body or of the at least one plastic material.

The inflow opening is the opening of the gas infeed hose through which the flushing gas or the flushing liquid flows from the gas infeed hose into the interior space of the hollow body. The outflow opening is accordingly the opening of the gas discharge hose through which the flushing gas or the flushing liquid flows into the gas discharge hose from the interior space of the hollow body.

The inflow opening of the gas infeed hose is arranged at a first end of the hollow body and the outflow opening is arranged at a second end of the hollow body opposite the first end.

The residence time of the through-flowing flushing gas or of the through-flowing flushing liquid against the internal wall of the hollow body or against the internal wall of the at least one plastic material is thereby increased and gas exchange through the hollow body or the at least one plastic material improved.

Furthermore, the gas infeed hose and the gas discharge hose are arranged in places coaxially to one another, wherein the two are preferably guided jointly out of the hollow body through a feedthrough.

In this way, there is only one point of access to the hollow body and only one common passage to the treatment position, thereby reducing the risk of microbial contamination at the point of transition of the coaxial gas infeed hose and gas discharge hose from the outside of the organism to the inside. As an alternative to coaxial hoses, it is possible to use a hose which is divided by a partition into two hoses, for example into two half moon-shaped or semicircular hoses.

The gas infeed hose and the gas discharge hose are connected to one another, wherein the gas infeed hose and the gas discharge hose preferably have a common outer hose and wherein the common outer hose is particularly preferably subdivided by a partition which borders the gas infeed hose on one side and the gas discharge hose on the other side.

A partition likewise particularly preferably subdivides the common outer hose into two cross-sectionally half moon-shaped or semicircular hoses which form the gas infeed hose and the gas discharge hose.

The risk of microbial contamination is also thereby reduced.

According to a preferred further development of the present invention, a sterile filter which is impermeable to microbes but permeable to gases is arranged in the gas infeed hose and/or the gas discharge hose.

This reduces the risk of infection for the treated patient and the attending personnel.

Moreover, a valve is arranged in the gas infeed hose and/or the gas discharge hose, wherein preferably the gas infeed hose and or/the gas discharge hose is capable of being shut off with the valve.

The expanded state (inflated state) of the hollow body may thereby be maintained, optionally even on removal of the flushing gas supply or the flushing liquid supply.

The sterile filter is arranged in the gas infeed hose or the gas discharge hose downstream of the valve in the direction of flow or the sterile filters are arranged in the gas infeed hose and in the gas discharge hose downstream of the valves.

In this way, the risk of infection for the treated patient and for the attending personnel may likewise be reduced.

Moreover, the valve is arranged in the gas infeed hose and configured as a one-way valve.

In this way, automatic gas-tight closure of the gas infeed hose is achieved on disconnection of the flushing gas supply or of the flushing liquid supply, without a valve having to be operated manually. Application safety of the medical placeholder is improved significantly thereby. It is additionally possible, on expansion of the hollow body with overpressure, to prevent the pressure from escaping from the hollow body through the gas infeed hose.

The valve is arranged in the gas discharge hose and configured as a pressure relief valve, wherein the opening pressure of the pressure relief valve is preferably adjustable.

The expanded state of the hollow body may thereby be reliably achieved.

The gas infeed hose and the gas discharge hose consist of a material which is impermeable to oxygen and carbon dioxide, preferably a plastic material impermeable to oxygen and carbon dioxide.

In this way, the oxygen is prevented from exiting prematurely from the flushing gas or the flushing liquid. In addition, the gas infeed hose and the gas discharge hose may in this way be made of an inexpensive plastic material.

Moreover, the hollow body or the at least one plastic material of the hollow body contain at least one antiseptic active ingredient or are coated with at least one antiseptic active ingredient.

In this way, the surface of the medical placeholder and the surroundings of the medical placeholder in the patient's body may be disinfected with the at least one antiseptic active ingredient. In this way, treatment complications are avoided.

Moreover, feedthroughs are arranged in at least one wall of the hollow body or of the at least one plastic material of the hollow body, the feedthroughs having openings pointing in the direction of the outside of the hollow body and connecting at least one duct with the surroundings of the hollow body in a manner permeable to liquids and gases, wherein the at least one duct is provided for feeding liquids into the hollow body to the feedthroughs, wherein the at least one duct is preferably connected with a feed hose for pharmaceutical active ingredient solutions, wherein a connection adapter, in particular a Luer Lock adapter, is particularly preferably arranged at the feed hose.

This makes it possible to connect the feedthroughs with the feed hose through which antiseptic or antibiotic solutions may be forced into the feedthroughs. The feedthroughs enable antimicrobial protection of the surface of the hollow body. It is also possible to introduce liquid or gel-type antibiotic or antiseptic pharmaceutical preparations into the feedthroughs which may migrate through diffusion into the surroundings and so be used to treat the patient in the region of the medical placeholder.

Furthermore, the hollow body rests in the uninflated state against the gas infeed hose and/or against the gas discharge hose, wherein the hollow body or the at least one plastic material is preferably inflatable in the manner of a balloon.

In this way, the medical placeholder is compact when not inflated (in the unexpanded state) and may thus be more easily introduced into the bone defect and removed again from the bone defect.

The objects underlying the present invention are also achieved by a method for gas-flushing a surface of a medical placeholder, in particular a medical placeholder according to the invention, having the following steps:

A) expanding a hollow body by feeding a flushing liquid or a flushing gas containing oxygen into an interior space of the hollow body, thereby enlarging the interior space of the hollow body;
B) delivering gaseous oxygen from the flushing liquid or the flushing gas through a plastic material defining the interior space to the surroundings of the hollow body;
C) absorbing gaseous carbon dioxide from the surroundings of the hollow body through the plastic material defining the interior space into the flushing liquid or the flushing gas;
D) passing the flushing liquid or the flushing gas through the interior space of the hollow body and discharging the flushing liquid or flushing gas out of the interior space.

Steps B) and C) preferably run simultaneously. In addition, the gas exchange in steps B) and C) preferably also takes place as early as during step A) and throughout step D).

Air or oxygen may be used as flushing gas. It also falls within the purposes of the invention if, instead of air or oxygen as the flushing gas, oxygen-saturated flushing liquids, such as for example physiological saline, Ringer's solution or Ringer's lactate solution, are introduced into the expandable medical placeholder, in particular by the gas infeed hose. It is furthermore also possible to use perfluorinated decalin or other perfluorinated flushing liquids in which oxygen is soluble as the oxygen carrier. These flushing liquids may be discharged from the hollow body by the gas discharge hose.

The flushing liquid may contain gaseous oxygen ($O_2$ molecules). The gaseous oxygen may be dissolved in the flushing liquid such that it can emerge from the flushing liquid through the plastic material into the surroundings of the hollow body.

The method is not to be performed for medical treatment of a human or animal body.

Preferably, the method is to be performed outside a human or an animal body.

The method according to the invention is not to be performed by a doctor or a physician.

Preferably and furthermore, the hollow body is introduced into a cavity prior to step A), wherein during step A) the shape of the inflated hollow body adapts at least in places to the shape of the cavity and during steps B) and C) rests at least in places against the cavity.

The cavity is preferably not a cavity of a human or animal body.

Through introduction into the cavity the advantages of the method are brought fully into play. The gas exchange between the cavity and the interior space of the hollow body brings about the advantages according to the invention.

Moreover, the hollow body is inflated in step A) until a minimum pressure is reached, wherein a pressure relief valve opens once the minimum pressure is reached, the flushing liquid or the flushing gas being discharged through this pressure relief valve from the interior space of the hollow body during step D).

In this way, the shape of the hollow body may be adapted to a surrounding shape, such that the surroundings of the hollow body may be mechanically stabilized with the hollow body.

Underlying the invention are the surprising findings that the expandable medical placeholder makes it possible to assist in the construction of a connective tissue membrane, in that the medical placeholder is adaptable to the shape of the bone defect and in that the connective tissue membrane is supplied with oxygen and over-acidification of the connective tissue membrane by carbon dioxide or carbonic acid is avoided. At the same time, the medical placeholder may be more easily removed after volumetric contraction through a small cut in the connective tissue membrane. For these reasons, more rapid and effective ossification can be achieved, such that successful healing may take place sooner. The particular advantage is also that the inside, remote from the bloodstream, of the connective tissue layer, which can normally be supplied only poorly with oxygen by the bloodstream, can be better supplied using the medical placeholder according to the invention as the latter directly adjoins the connective tissue layer. This is not possible with conventional solid placeholders.

An advantage of the medical placeholder according to the invention consists thus in the fact that the hollow body can be adapted in shape by expansion (for example by inflation) to match the bone defect to be filled. It is furthermore advantageous that, after completion of the implantation phase, the hollow body can reduce its volume through application of a vacuum, thereby enabling removal of the hollow body through a small opening in the connective tissue membrane formed, such that the connective tissue membrane remains largely undamaged. A significant advantage of the medical placeholder according to the invention is supply of the cells of the forming connective tissue membrane with oxygen and removal of the carbon dioxide arising. In this way, an oxygen deficiency is enabled even in the case of soft tissue coverage with previously damaged soft tissue. Removal of the carbon dioxide prevents acidification of the cells of the forming connective tissue membrane. These two processes assist in formation of a viable connective tissue membrane.

It is essential for ossification that the vascularized connective tissue membrane is sufficiently viable and is supplied with oxygen and nutrients by the overlying soft tissue.

It was identified, in the context of the present invention, that during the implantation period of conventional bone cement spacers the forming connective tissue membrane is supplied with oxygen and nutrients substantially by the overlying soft tissue. Removal of the carbon dioxide arising during the metabolic process likewise proceeds via the overlying soft tissue. If only thin soft tissue is present or the soft tissue has been previously damaged when the bone defect arose, delayed formation of the connective tissue membrane should be expected due to inadequate oxygen and nutrient supply and insufficient removal of carbon dioxide. It is desirable reliably to generate a connective tissue membrane even in the case of low soft tissue coverage or even in the case of soft tissue coverage with previously damaged soft tissue. To this end, the cells which are located immediately at the spacer surface should be optimally supplied with oxygen. Furthermore, the carbon dioxide arising needs to be removed in order prevent the local pH from falling. A fall in pH can cause cell damage.

An exemplary expandable medical placeholder according to the invention may have:
a) at least one expandable plastic hollow body with an interior space,
b) at least one gas infeed hose, which is connected in a gas-permeable manner with the interior space of the plastic hollow body,
c) at least one gas discharge hose, which is connected in a gas-permeable manner with the interior space of the plastic hollow body, and
d) wherein the plastic hollow body has a permeability coefficient for oxygen of greater than or equal to 0.5 $cm^3/(m^2*d*bar)$ and a permeability coefficient for carbon dioxide of greater than or equal to 0.5 $cm^3/(m^2*d*bar)$.

It is to be understood that both the foregoing general description and the following detailed description are exemplary, but are not restrictive, of the disclosure.

BRIEF DESCRIPTION OF THE DRAWING

Six further exemplary embodiments of the invention are explained below with reference to nineteen schematically depicted figures, but without thereby restricting the invention. In the figures.

DETAILED DESCRIPTION OF THE DISCLOSURE

In FIGS. 1 to 17, the front of the respective medical placeholder is oriented downwards and the rear upwards.

Figure 1:
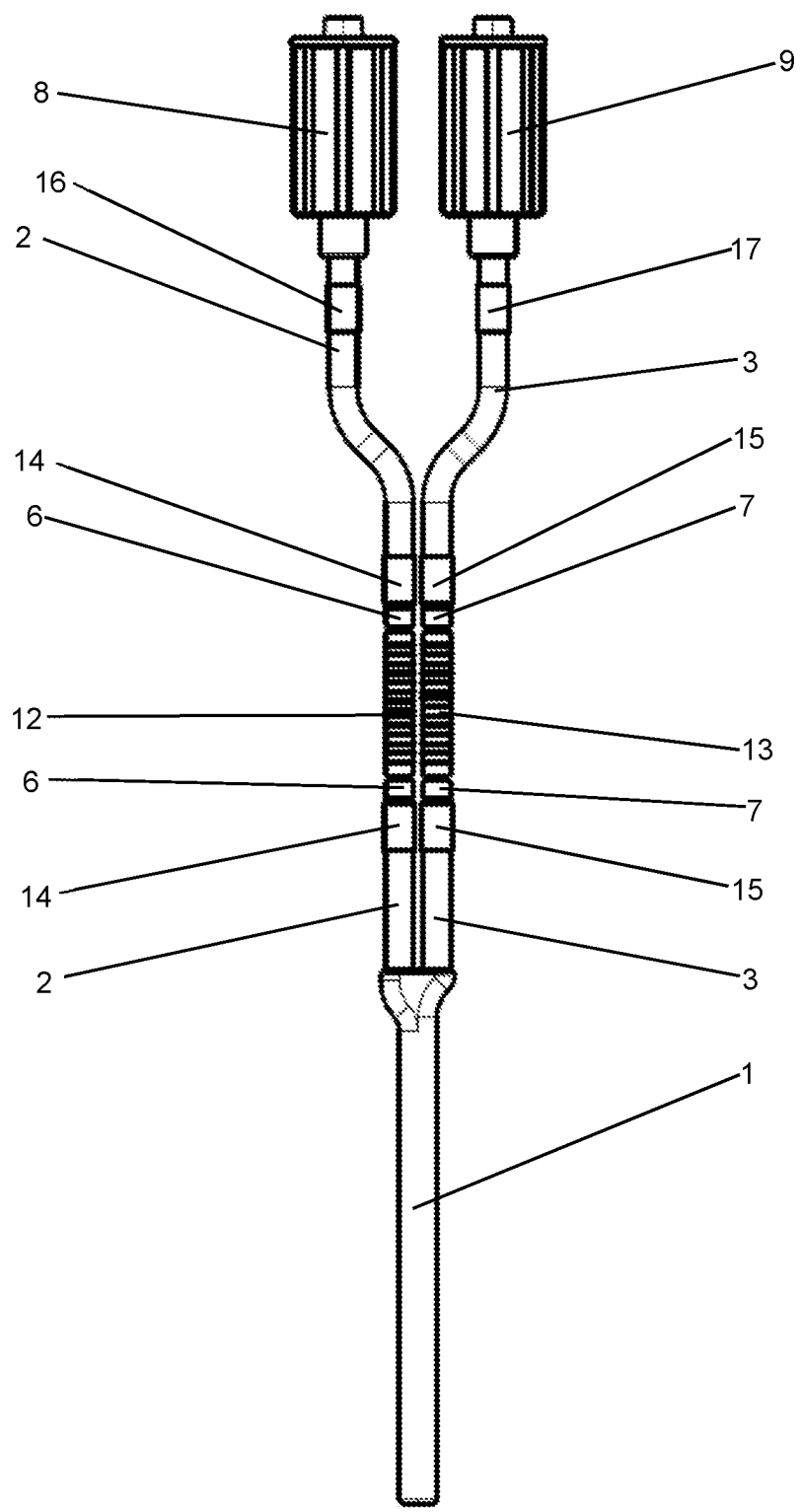
FIG. 1 is a schematic plan view of a first exemplary medical placeholder according to the invention in the compressed state.
Figure 2:
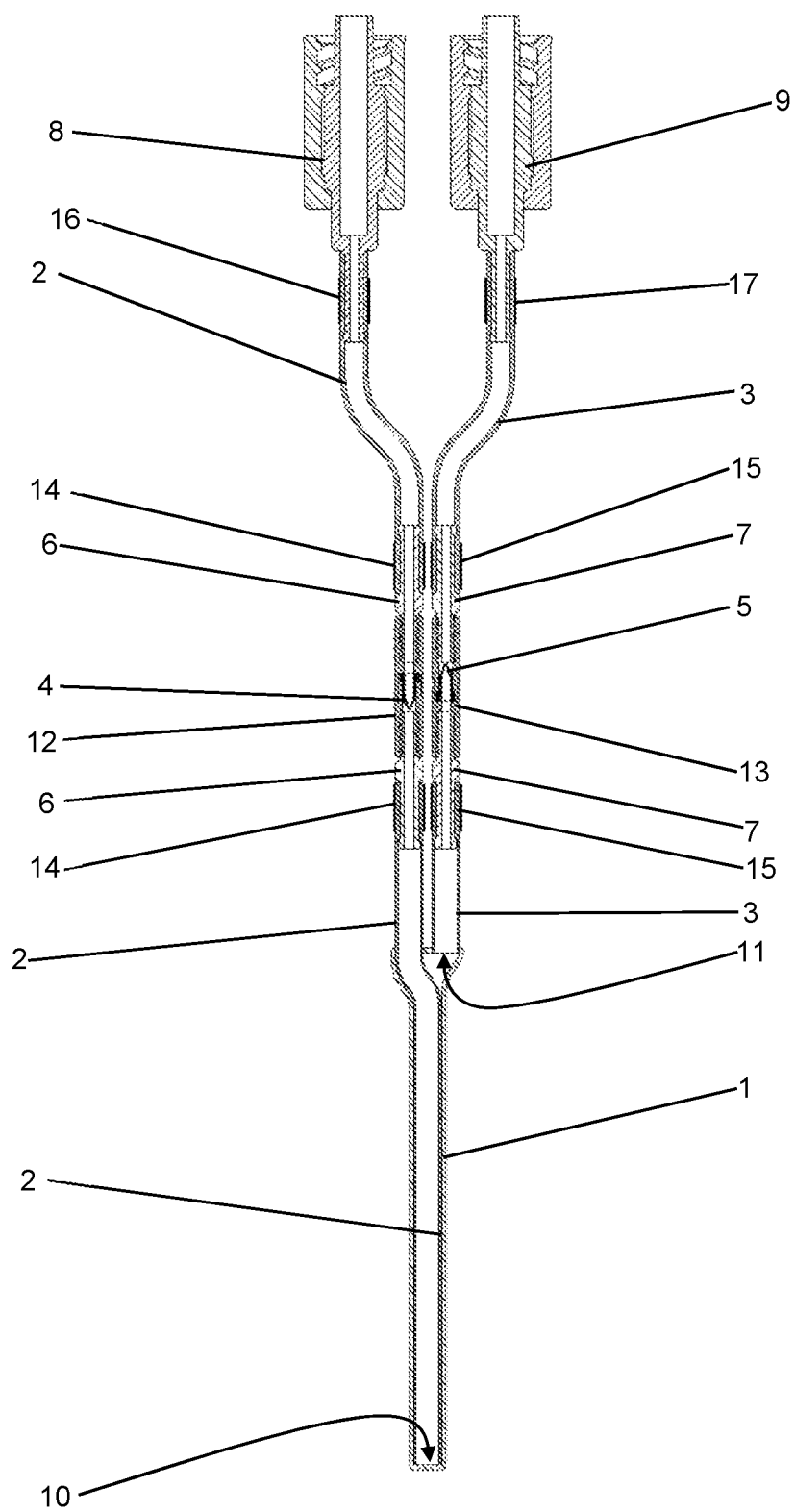
FIG. 2 is a schematic cross-sectional view of the first exemplary medical placeholder according to FIG. 1 in the compressed state, wherein the section plane lies in the image plane of FIG. 1.
Figure 3:
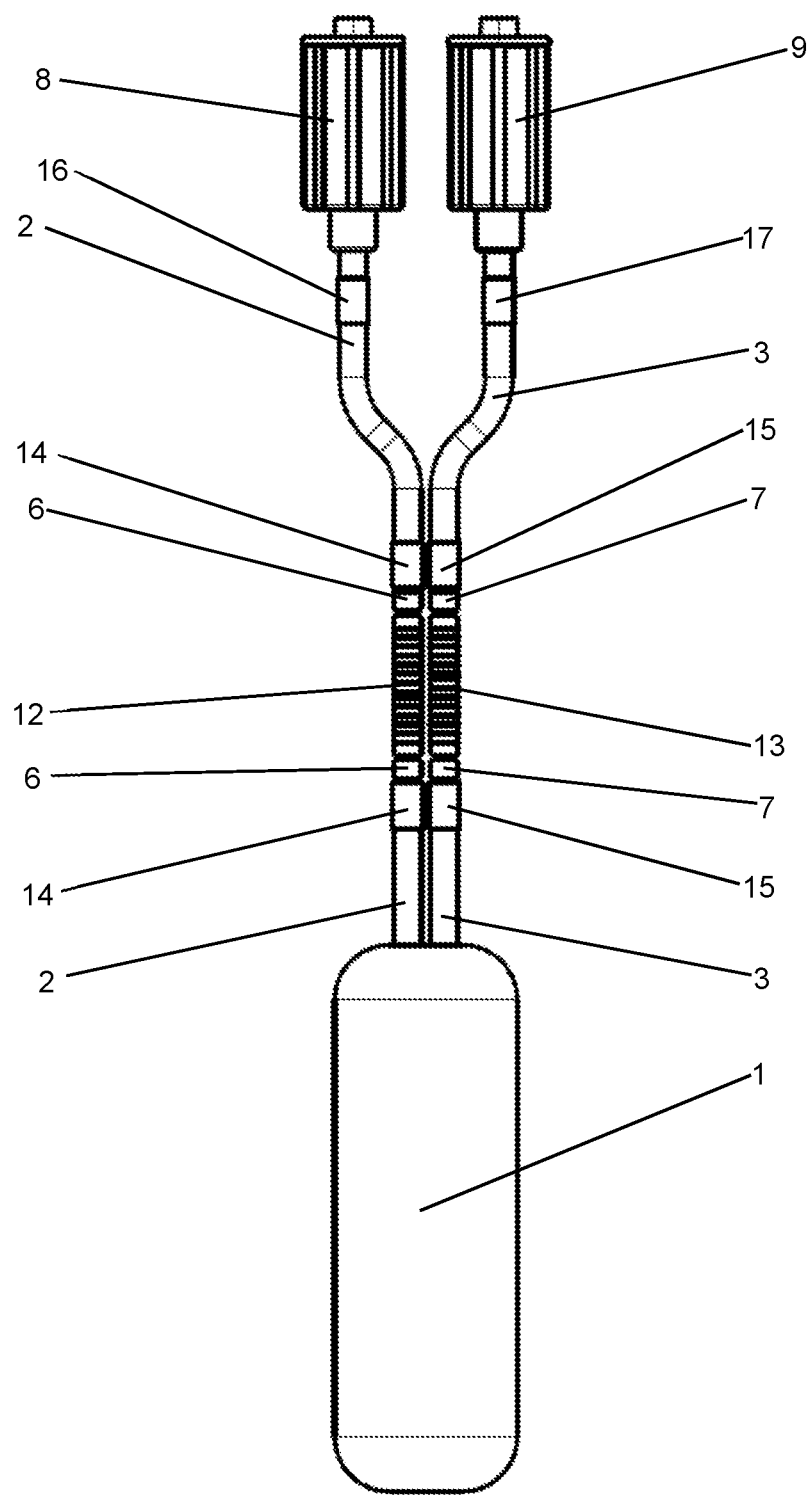
FIG. 3 is a schematic plan view of the first exemplary medical placeholder according to FIGS. 1 and 2 in the expanded state.
Figure 4:
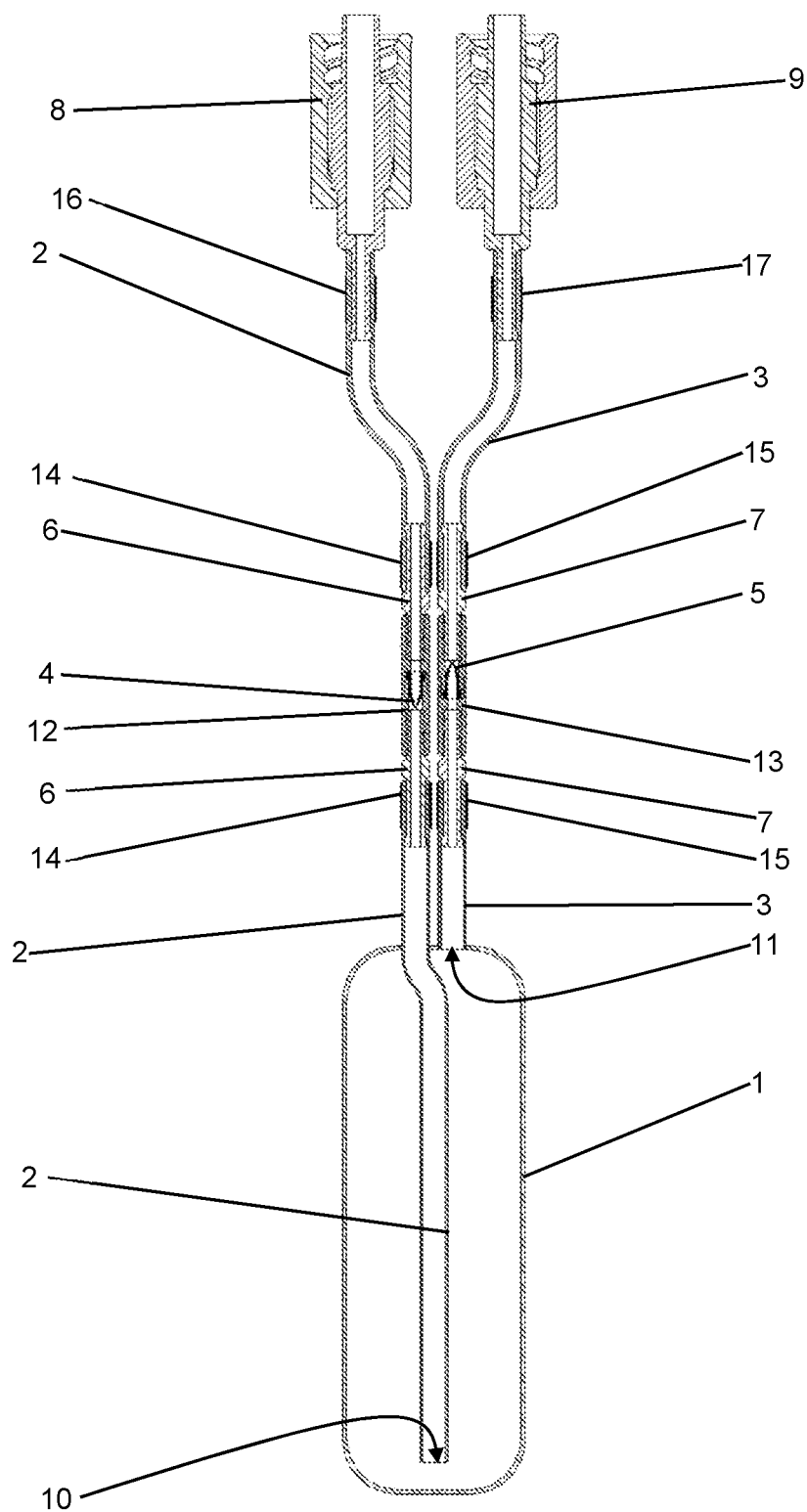
FIG. 4 is a schematic cross-sectional view of the medical placeholder according to FIGS. 1 to 3 in the expanded state, wherein the section plane lies in the image plane of FIG. 3.
Figure 5:
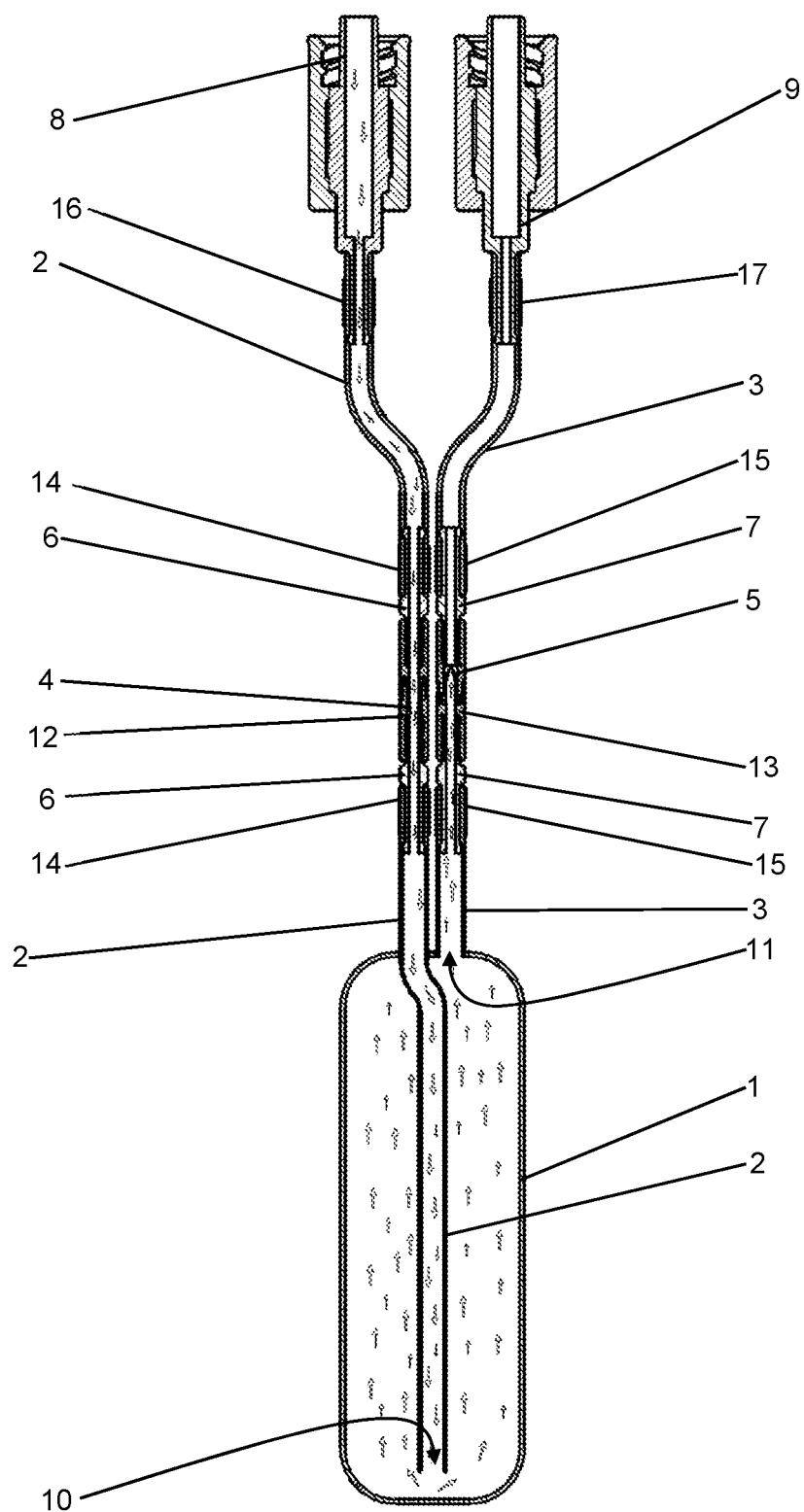
FIG. 5 shows the schematic cross-sectional view according to FIG. 4, wherein the flow conditions are indicated with arrows.

FIGS. 1 to 5 show illustrations of a first medical placeholder according to the invention. FIGS. 1 and 2 show the placeholder in the compressed state and FIGS. 3 to 5 show the placeholder in the expanded state.

The first medical placeholder according to the invention has a hollow body 1 of an elastically or plastically deformable plastic material. The hollow body 1 is expandable, in that it is inflated with a flushing gas or in that a flushing liquid is forced under pressure into the hollow body 1. The hollow body 1 for example consists of a rubber.

The material used for the hollow body 1 is permeable to gaseous molecular oxygen and to gaseous carbon dioxide. The hollow body 1 or the material from which the hollow body 1 is made to this end has a permeability coefficient for oxygen of greater than or equal to 0.5 $cm^3/(m^2*d*bar)$ and a permeability coefficient for carbon dioxide of greater than or equal to 0.5 $cm^3/(m^2*d*bar)$. The permeability coefficient is determined pursuant to DIN 53380-4 (11/2006).

For feeding in of a flushing fluid (a flushing gas or a flushing liquid), an interior space of the hollow body 1 is connected with a gas infeed hose 2 of plastic material. For discharge of the flushing fluid (the flushing gas or flushing liquid) from the hollow body 1, the interior space of the hollow body 1 is connected with a gas discharge hose 3 of plastic material. The gas infeed hose 2 and the gas discharge hose 3 are flexible and movable at least in places. A valve 4 in the form of a lip valve is arranged in the gas infeed hose 2, the valve 4 allowing flow of the flushing fluid toward the hollow body 1 but preventing flow of the flushing fluid away from the hollow body 1. A valve 5 in the form of a lip valve is arranged in the gas discharge hose 3, the valve 5 preventing flow of the flushing fluid toward the hollow body 1 but allowing flow of the flushing fluid away from the hollow body 1. The valve 5 is configured to open from a minimum pressure of the flushing fluid. The minimum pressure is preferably adjustable at the valve 5. The minimum pressure may in this respect be selected such that the pressure of the flushing fluid is sufficient to transfer the hollow body 1 from the compressed state (see FIGS. 1 and 2) to the expanded state (see FIGS. 3 to 5).

The valves 4, 5 are connected with the gas infeed hose 2 and the gas discharge hose 3 via connecting sleeves 6, 7. To this end, the gas infeed hose 2 is slipped onto the connecting sleeve 6 and fastened there with a crimping sleeve 14. The gas discharge hose 3 is likewise slipped onto the connecting sleeve 7 and fastened there with a crimping sleeve 15.

The gas infeed hose 2 ends at its rear in an adapter 8 in the form of a Luer Lock adapter. The gas discharge hose 3 likewise ends at its rear in an adapter 9 in the form of a Luer Lock adapter. The flushing fluid is fed in and discharged through the adapters 8, 9.

The gas infeed hose 2 mleads via an inflow opening 10 into the front part of the interior of the hollow body 1, while the gas discharge hose 3 is connected with the interior space of the hollow body 1 via an outflow opening 11 at the opposing rear of the interior space of the hollow body 1. In this way, it is ensured that the flushing fluid can flow along the surface of the wall of the entire hollow body 1 and gas exchange of oxygen and carbon dioxide can thereby take place through the wall over the entire length of the hollow body 1.

The valve 4 has a valve housing 12. The valve housing 12 is connected via an internal thread to external threads of the connecting sleeve 6. The valve 5 has a valve housing 13. The valve housing 13 is connected via an internal thread to external threads of the connecting sleeve 7. All the connections are gas-tight and pressure-tight.

The gas infeed hose 2 is slipped onto a connecting port of the adapter 8 and fastened pressure-tightly and gas-tightly thereon with a crimping sleeve 16. The gas discharge hose 3 is slipped onto a connecting port of the adapter 9 and fastened pressure-tightly and gas-tightly thereon with a crimping sleeve 17.

In the compressed state, the hollow body 1 may also be introduced into a cavity through a small opening. The hollow body 1 may be expanded therein and in this way the external shape of the hollow body 1 may be adapted to the cavity. The expanded hollow body 1, or the placeholder in the expanded state, thus mechanically supports and stabilizes the cavity. If the placeholder is no longer needed, the hollow body 1 is transferred back into the compressed state, for example by being evacuated. The hollow body 1 is then removed from the cavity through a narrow opening. If, in particular, the cavity is a cavity in a bone, this bone defect may in this way be carefully treated.

When in operation, the flushing fluid is fed into the medical placeholder through the adapter 8. The flushing fluid flows through the gas infeed hose 2 and opens the valve 4 when pressure is sufficient. The flushing fluid then flows through the inflow opening 10 into the hollow body 1 and through the hollow body 1. The flushing fluid flows through the gas discharge hose 3 to the initially closed valve 5. A pressure then builds up in the interior of the hollow body 1, by which the hollow body 1 is transferred into the expanded state (see FIG. 5). As soon as the pressure is sufficient at the valve 5 in the gas discharge hose 3, the valve 5 opens and the flushing fluid flows out through the gas discharge hose 3 and the adapter 9.

Oxygen is contained in the flushing fluid. The flushing fluid discharges oxygen through the wall of the hollow body 1 to the surroundings of the hollow body 1. At the same time, the flowing flushing fluid absorbs carbon dioxide, which diffuses through the wall of the hollow body 1 into the interior space, from the surroundings of the hollow body 1 and conveys the carbon dioxide away from the medical placeholder through the adapter 9. In this way, the surroundings of the hollow body 1 are supplied with oxygen and the absorption of carbon dioxide prevents over-acidification of the surroundings of the hollow body 1.

In the gas infeed hose 2 and/or in the gas discharge hose 3, it is also preferably possible to arrange sterile filters 19 which are impermeable to microbes but permeable to gases. Microbes which might otherwise reach the hollow body 1 and/or might be conveyed away from the hollow body 1 through the adapter 9 may be removed from the flushing fluid with the sterile filter 19. This reduces the risk of infection for the treated patient and the attending personnel.

The sterile filter 19 may preferably be arranged in the gas infeed hose 2 or the gas discharge hose 3 downstream of the valve 4 or the valve 5 in the direction of flow or the sterile filters 19 may be arranged in the gas infeed hose 2 and in the gas discharge hose 3 downstream of the valves 4, 5.

The hollow body 1 and the adjoining regions of the hoses 2, 3 are coated with an antiseptic substance or a soluble antiseptic substance is contained in the material of the hollow body 1, in order to prevent an infection.

To treat the surroundings of the hollow body 1, feedthroughs 18 are arranged in at least one wall of the hollow body 1 or of the at least one plastic material of the hollow body 1, the feedthroughs 18 having openings pointing in the direction of the outside of the hollow body 1, the openings connecting at least one duct (not shown) with the surroundings of the hollow body 1 in a manner permeable to liquids and gases. The at least one duct may be provided for feeding liquids into the hollow body 1 to the feedthroughs 18. In addition, the at least one duct may be connected with a feed hose (not shown) for pharmaceutical active ingredient solutions. In this way a pharmaceutical active ingredient solution can be delivered at the surface of the hollow body 1.

Figure 6:
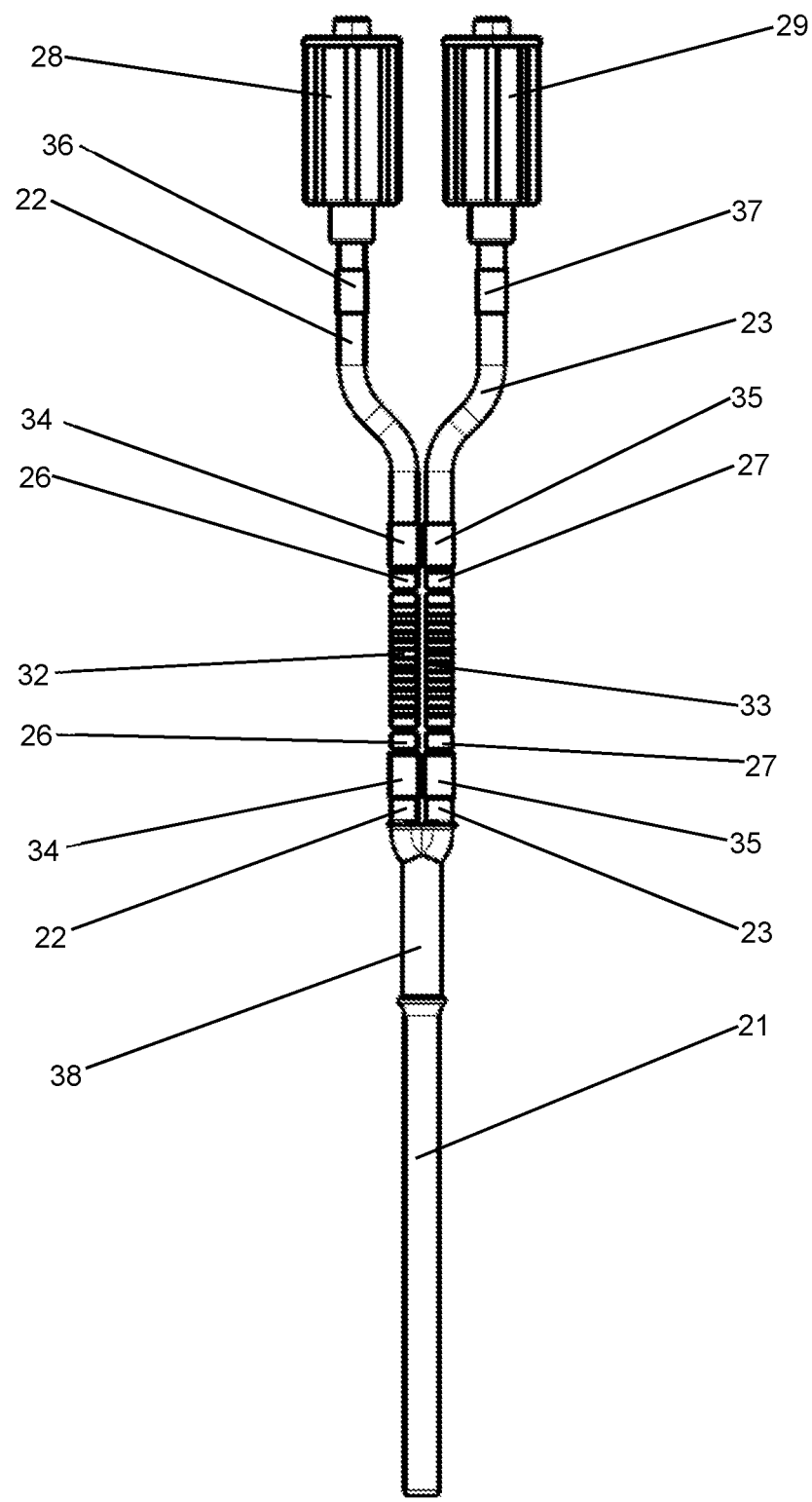
FIG. 6 is a schematic plan view of a second exemplary medical placeholder according to the invention in the compressed state.
Figure 7:
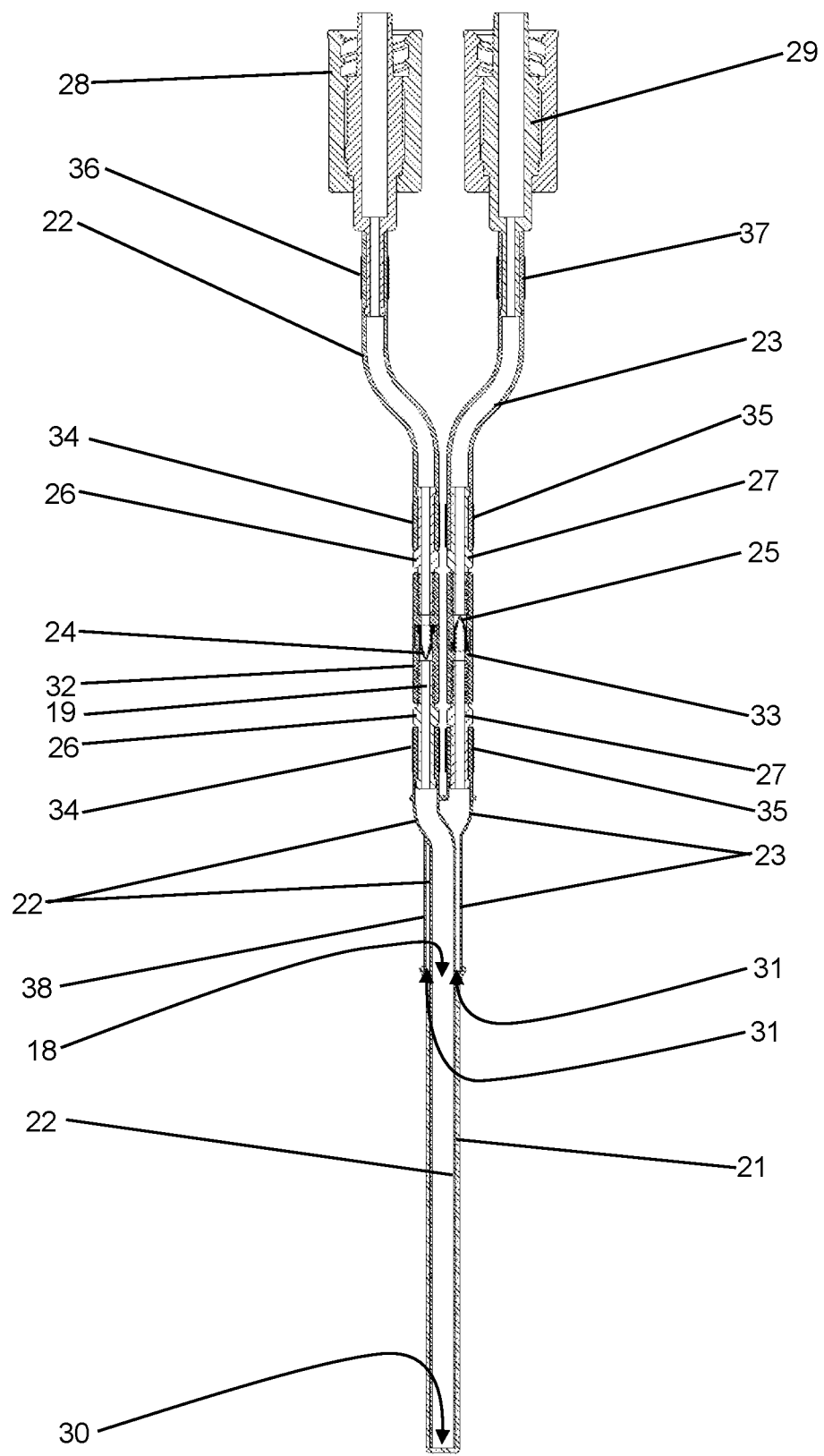
FIG. 7 is a schematic cross-sectional view of the second exemplary medical placeholder according to FIG. 6 in the compressed state, wherein the section plane lies in the image plane of FIG. 6.
Figure 8:
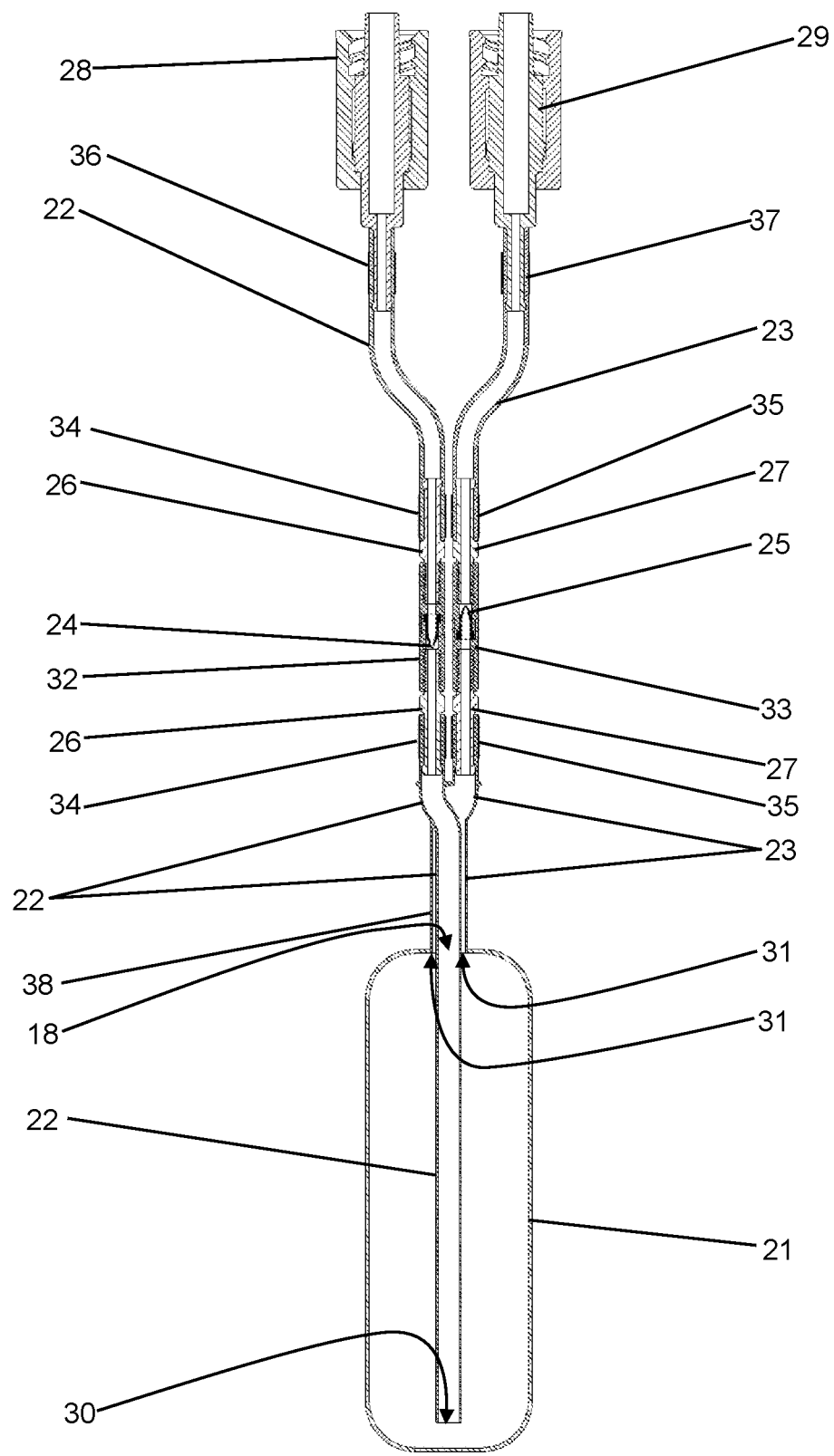
FIG. 8 is a schematic cross-sectional view of the second exemplary medical placeholder according to FIGS. 6 and 7 in the expanded state.
Figure 9:
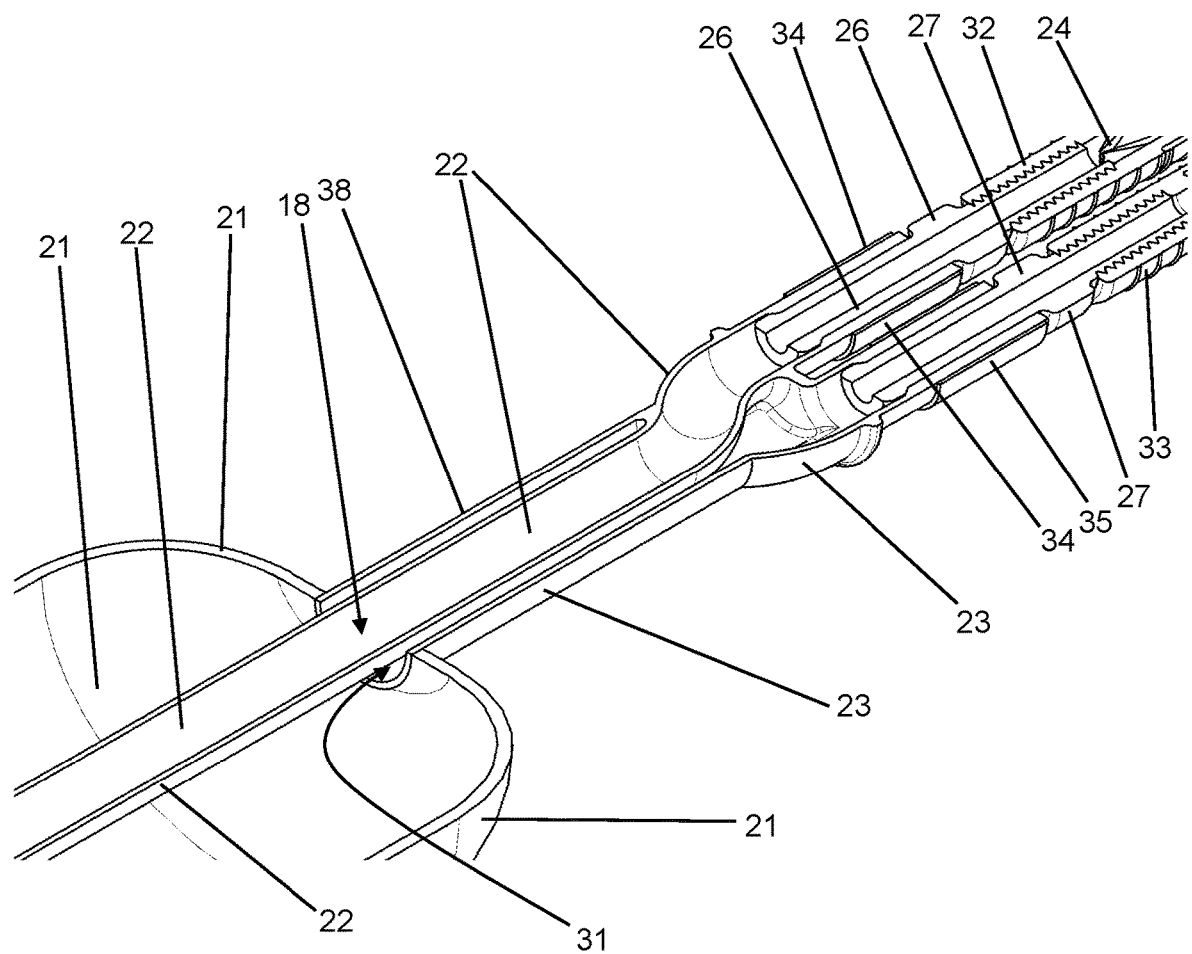
FIG. 9 is a schematic perspective partial cross-sectional view of the second exemplary medical placeholder according to FIGS. 6 to 8 in the expanded state, wherein the section plane lies in the image plane of FIG. 6.

FIGS. 6 to 9 show illustrations of a second medical placeholder according to the invention. FIGS. 6 and 7 show the placeholder in the compressed state and FIGS. 8 and 9 show the placeholder in the expanded state.

The second medical placeholder according to the invention has a hollow body 21 of an elastically or plastically deformable plastic material. The hollow body 21 is expandable, in that it is inflated with a flushing gas or in that a flushing liquid is forced under pressure into the hollow body 21. The hollow body 21 for example consists of a rubber.

The material used for the hollow body 21 is permeable to gaseous molecular oxygen and to gaseous carbon dioxide. The hollow body 21 or the material from which the hollow body 21 is made to this end has a permeability coefficient for oxygen of greater than or equal to 0.5 cm$^3$/(m$^2$*d*bar) and a permeability coefficient for carbon dioxide of greater than or equal to 0.5 cm$^3$/(m$^2$*d*bar). The permeability coefficient is determined pursuant to DIN 53380-4 (11/2006).

For feeding in of a flushing fluid (a flushing gas or a flushing liquid), an interior space of the hollow body 21 is connected with a gas infeed hose 22 of plastic material. For discharge of the flushing fluid (the flushing gas or flushing liquid) from the hollow body 21, the interior space of the hollow body 21 is connected with a gas discharge hose 23 of plastic material. The gas infeed hose 22 and the gas discharge hose 23 are flexible and movable at least in places. A valve 24 in the form of a lip valve is arranged in the gas infeed hose 22, the valve 24 allowing flow of the flushing fluid toward the hollow body 21 but preventing flow of the flushing fluid away from the hollow body 21. A valve 25 in the form of a lip valve is arranged in the gas discharge hose 23, the valve 25 preventing flow of the flushing fluid toward the hollow body 21 but allowing flow of the flushing fluid away from the hollow body 21. The valve 25 is configured to open from a minimum pressure of the flushing fluid. The minimum pressure is preferably adjustable at the valve 25. The minimum pressure may in this respect be selected such that the pressure of the flushing fluid is sufficient to transfer the hollow body 21 from the compressed state (see FIGS. 6 and 7) to the expanded state (see FIGS. 8 and 9).

The valves 24, 25 are connected with the gas infeed hose 22 and the gas discharge hose 23 via connecting sleeves 26, 27. To this end, the gas infeed hose 22 is slipped onto the connecting sleeve 26 and fastened there with a crimping sleeve 34. The gas discharge hose 23 is likewise slipped onto the connecting sleeve 27 and fastened there with a crimping sleeve 35.

The gas infeed hose 22 ends at its rear in an adapter 28 in the form of a Luer Lock adapter. The gas discharge hose 23 likewise ends at its rear in an adapter 29 in the form of a Luer Lock adapter. The flushing fluid is fed in and discharged through the adapters 28, 29.

The gas infeed hose 22 leads via an inflow opening 30 into the front part of the interior of the hollow body 21, while the gas discharge hose 23 is connected with the interior space of the hollow body 21 via an outflow opening 31 at the opposing rear of the interior space of the hollow body 21. In this way, it is ensured that the flushing fluid can flow along the surface of the wall of the entire hollow body 21 and gas exchange of oxygen and carbon dioxide can thereby take place through the wall over the entire length of the hollow body 21.

The valve 24 has a valve housing 32. The valve housing 32 is connected via an internal thread to external threads of the connecting sleeve 26. The valve 25 has a valve housing 33. The valve housing 33 is connected via an internal thread to external threads of the connecting sleeve 27. All the connections are gas-tight and pressure-tight.

The gas infeed hose 22 is slipped onto a connecting port of the adapter 28 and fastened pressure-tightly and gas-tightly thereon with a crimping sleeve 36. The gas discharge hose 23 is slipped onto a connecting port of the adapter 29 and fastened pressure-tightly and gas-tightly thereon with a crimping sleeve 37.

Unlike in the first exemplary embodiment, in the second exemplary embodiment the gas infeed hose 22 and the gas discharge hose 23 are brought together upstream of the hollow body 21 and there form a coaxial hose 38. In this case, the gas discharge hose 23 is arranged within the gas infeed hose 22 (as shown in FIGS. 6 to 9) or the gas infeed hose 22 is arranged within the gas discharge hose 23. The advantage is that only one connection is present in the form of a feedthrough 18 leading into the hollow body 21, such that the passage is easier to close and the risk of microbes passing therethrough is reduced. In addition, the outflow opening 31 leads around the gas infeed hose 22 into the interior space of the hollow body 21 (or alternatively the inflow opening 30 leads around the gas discharge hose into the interior space of the hollow body 21). In this way, the entire surface of the hollow body 21 is even more directly and readily coated by the flushing fluid and thus gas exchange improved.

When in operation, the flushing fluid is fed into the medical placeholder through the adapter 28. The flushing fluid flows through the gas infeed hose 22 and opens the valve 24 when pressure is sufficient. The flushing fluid then flows through the inflow opening 30 into the hollow body 21 and through the hollow body 21. The flushing fluid flows through the gas discharge hose 23 to the initially closed valve 25. A pressure then builds up in the interior of the hollow body 21, by which the hollow body 21 is transferred into the expanded state. As soon as the pressure is sufficient at the valve 25 in the gas discharge hose 23, the valve 25 opens and the flushing fluid flows out through the gas discharge hose 23 and the adapter 29.

In the compressed state, the hollow body 21 may also be introduced into a cavity through a small opening. The hollow body 21 may be expanded therein and in this way the external shape of the hollow body 21 may be adapted to the cavity. The expanded hollow body 21, or the placeholder in the expanded state, thus mechanically supports and stabilizes the cavity. If the placeholder is no longer needed, the hollow body 21 is transferred back into the compressed state, for example by being evacuated. The hollow body 21 is then removed from the cavity through a narrow opening. If, in particular, the cavity is a cavity in a bone, this bone defect may in this way be carefully treated.

Oxygen is contained in the flushing fluid. The flushing fluid discharges oxygen through the wall of the hollow body 21 to the surroundings of the hollow body 21. At the same time, the flowing flushing fluid absorbs carbon dioxide, which diffuses through the wall of the hollow body 21 into the interior space, from the surroundings of the hollow body 21 and conveys the carbon dioxide away from the medical placeholder through the adapter 29. In this way, the surroundings of the hollow body 21 are supplied with oxygen and the absorption of carbon dioxide prevents over-acidification of the surroundings of the hollow body 21.

In the gas infeed hose 22 and/or in the gas discharge hose 23, it is also preferably possible to arrange sterile filters 19 which are impermeable to microbes but permeable to gases. Microbes which might otherwise reach the hollow body 21 and/or might be conveyed away from the hollow body 21 through the adapter 29 may be removed from the flushing fluid with the sterile filter 19. This reduces the risk of infection for the treated patient and the attending personnel.

The sterile filter 19 may preferably be arranged in the gas infeed hose 22 or the gas discharge hose 23 downstream of the valve 24 or the valve 25 in the direction of flow or the sterile filters 19 may be arranged in the gas infeed hose 22 and in the gas discharge hose 23 downstream of the valves 24, 25.

The hollow body 21 and/or the coaxial hose 38 are coated with an antiseptic substance or a soluble antiseptic substance is contained in the material of the hollow body 21, in order to prevent an infection.

To treat the surroundings of the hollow body 21, feedthroughs 18 are arranged in at least one wall of the hollow body 21 or of the at least one plastic material of the hollow body 21, the feedthroughs 18 having openings pointing in the direction of the outside of the hollow body 21, the openings connecting at least one duct (not shown) with the surroundings of the hollow body 21 in a manner permeable to liquids and gases. The at least one duct may be provided for feeding liquids into the hollow body 21 to the feedthroughs 18. In addition, the at least one duct may be connected with a feed hose (not shown) for pharmaceutical active ingredient solutions. In this way a pharmaceutical active ingredient solution can be delivered at the surface of the hollow body 21.

Figure 10:
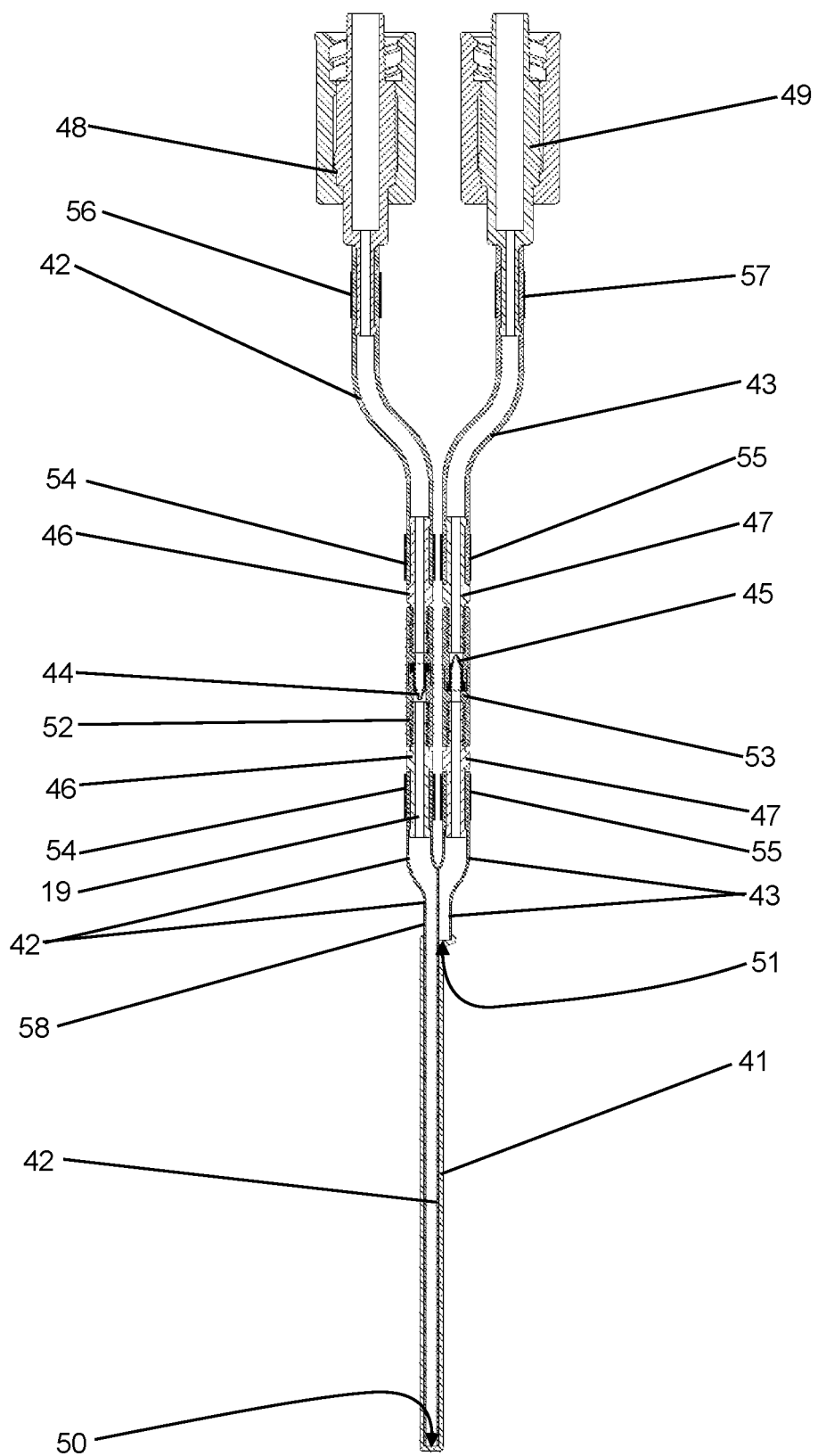
FIG. 10 is a schematic cross-sectional view of a third exemplary medical placeholder according to the invention in the compressed state.
Figure 11:
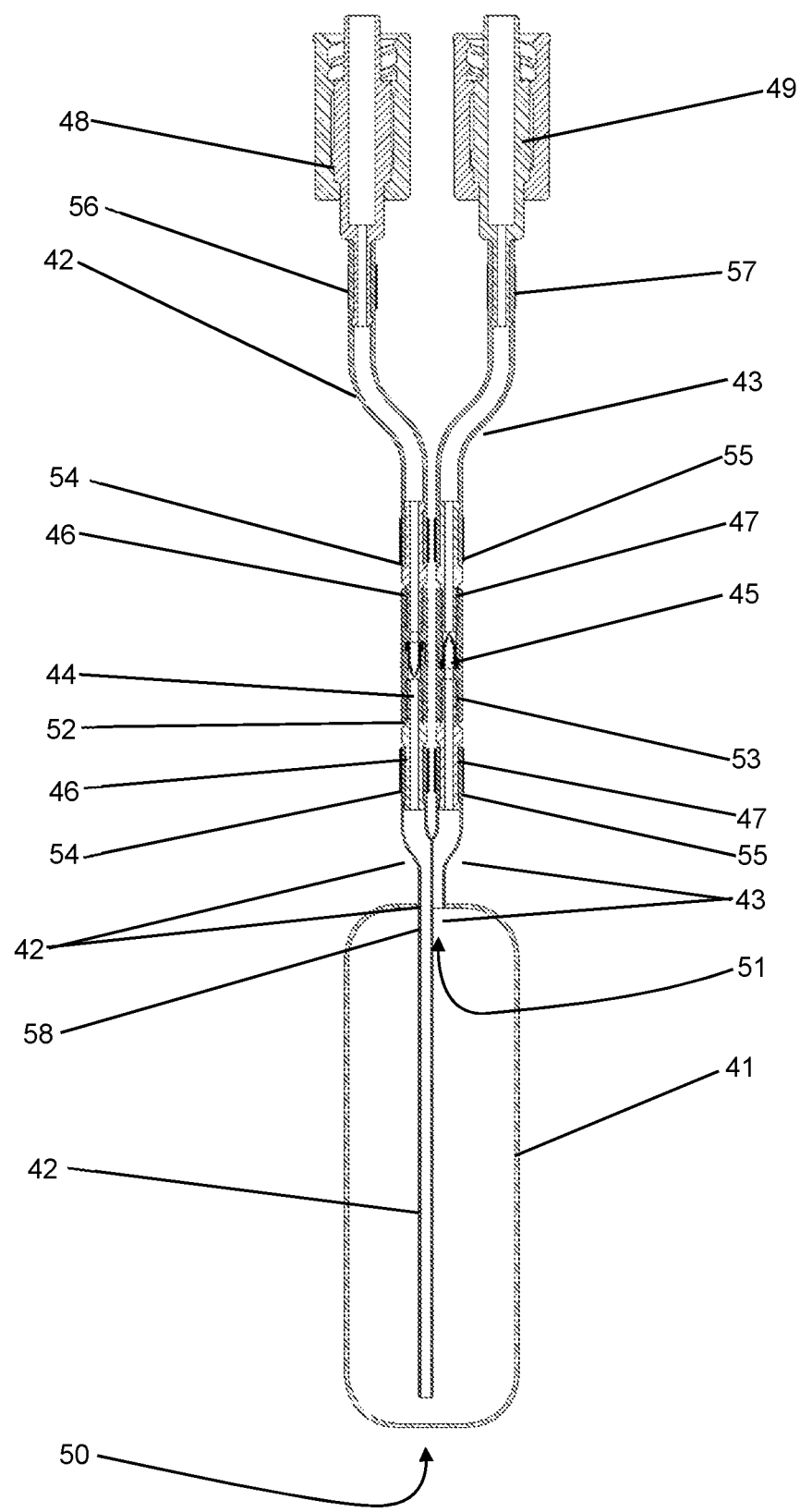
FIG. 11 is a schematic cross-sectional view of the third exemplary medical placeholder according to FIG. 10 in the expanded state.
Figure 12:
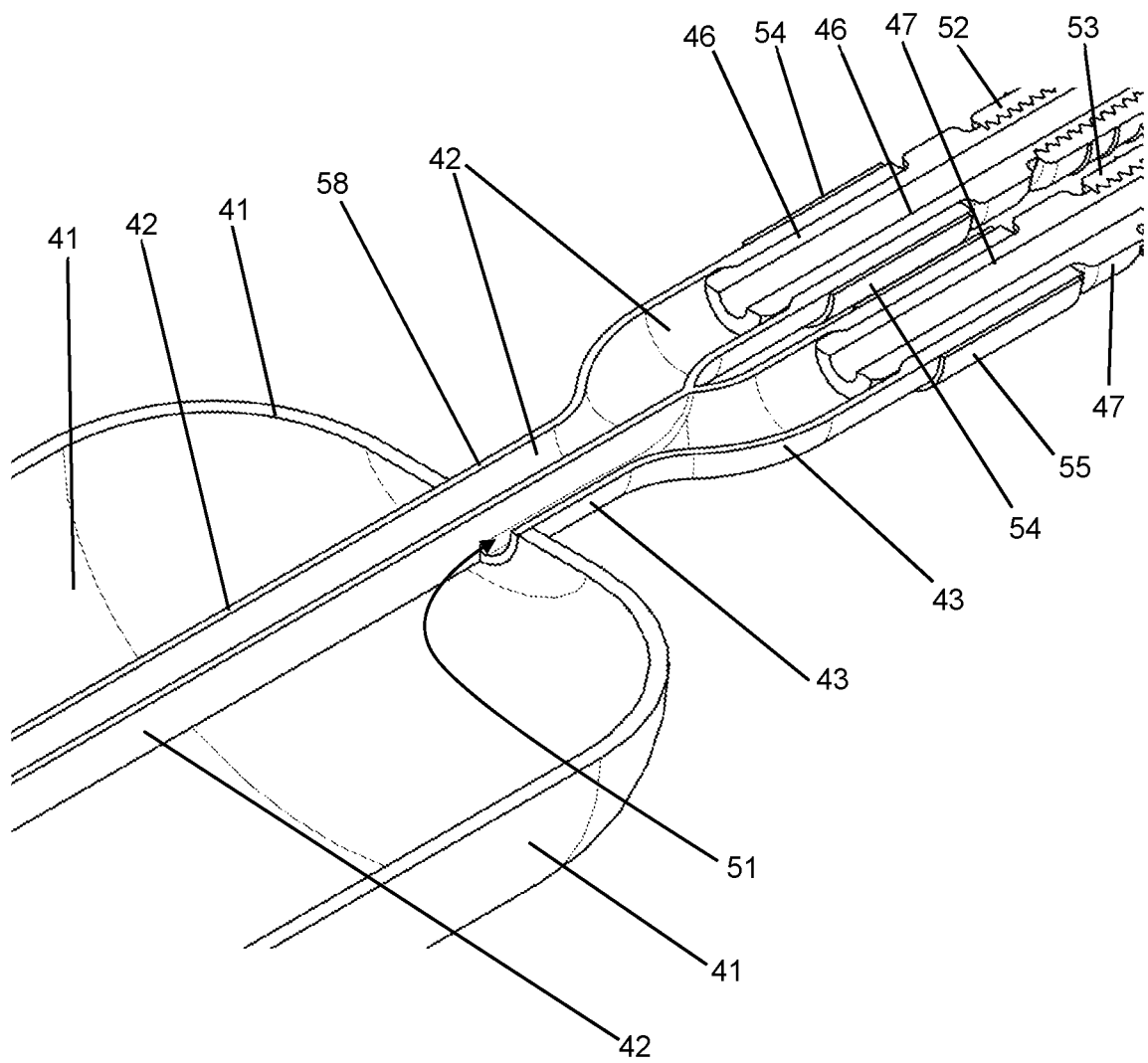
FIG. 12 shows a schematic perspective partial cross-sectional view of the third exemplary medical placeholder according to FIGS. 10 and 11 in the expanded state.

FIGS. 10 to 12 show illustrations of a third embodiment or example of a medical placeholder according to the invention. FIG. 10 shows the placeholder in the compressed state and FIGS. 11 and 12 show the placeholder in the expanded state.

The third medical placeholder according to the invention has a hollow body 41 of an elastically or plastically deformable plastic material. The hollow body 41 is expandable, in that it is inflated with a flushing gas or in that a flushing liquid is forced under pressure into the hollow body 41. The hollow body 41 for example consists of a rubber.

The material used for the hollow body 41 is permeable to gaseous molecular oxygen and to gaseous carbon dioxide. The hollow body 41 or the material from which the hollow body 41 is made to this end has a permeability coefficient for oxygen of greater than or equal to 0.5 $cm^3/(m^2*d*bar)$ and a permeability coefficient for carbon dioxide of greater than or equal to 0.5 $cm^3/(m^2*d*bar)$. The permeability coefficient is determined pursuant to DIN 53380-4 (11/2006).

For feeding in of a flushing fluid (a flushing gas or a flushing liquid), an interior space of the hollow body 41 is connected with a gas infeed hose 42 of plastic material. For discharge of the flushing fluid (the flushing gas or flushing liquid) from the hollow body 41, the interior space of the hollow body 41 is connected with a gas discharge hose 43 of plastic material. The gas infeed hose 42 and the gas discharge hose 43 are flexible and movable at least in places. A valve 44 in the form of a lip valve is arranged in the gas infeed hose 42, the valve 44 allowing flow of the flushing fluid toward the hollow body 41 but preventing flow of the flushing fluid away from the hollow body 41. A valve 45 in the form of a lip valve is arranged in the gas discharge hose 43, the valve 45 preventing flow of the flushing fluid toward the hollow body 41 but allowing flow of the flushing fluid away from the hollow body 41. The valve 45 is configured to open from a minimum pressure of the flushing fluid. The minimum pressure is preferably adjustable at the valve 45. The minimum pressure may in this respect be selected such that the pressure of the flushing fluid is sufficient to transfer the hollow body 41 from the compressed state (see FIG. 10) to the expanded state (see FIGS. 11 and 12).

The valves 44, 45 are connected with the gas infeed hose 42 and the gas discharge hose 43 via connecting sleeves 46, 47. To this end, the gas infeed hose 42 is slipped onto the connecting sleeve 46 and fastened there with a crimping sleeve 54. The gas discharge hose 43 likewise is slipped onto the connecting sleeve 47 and fastened there with a crimping sleeve 55.

The gas infeed hose 42 ends at its rear in an adapter 48 in the form of a Luer Lock adapter. The gas discharge hose 43 likewise ends at its rear in an adapter 49 in the form of a Luer Lock adapter. The flushing fluid is fed in and discharged through the adapters 48, 49.

The gas infeed hose 42 leads via an inflow opening 50 into the front part of the interior of the hollow body 41, while the gas discharge hose 43 is connected with the interior space of the hollow body 41 via an outflow opening 51 at the opposing rear of the interior space of the hollow body 41. In this way, it is ensured that the flushing fluid can flow along the surface of the wall of the entire hollow body 41 and gas exchange of oxygen and carbon dioxide can thereby take place through the wall over the entire length of the hollow body 41.

The valve 44 has a valve housing 52. The valve housing 52 is connected via an internal thread to external threads of the connecting sleeve 46. The valve 45 has a valve housing 53. The valve housing 53 is connected via an internal thread to external threads of the connecting sleeve 47. All the connections are gas-tight and pressure-tight.

The gas infeed hose 42 is slipped onto a connecting port of the adapter 48 and fastened pressure-tightly and gas-tightly thereon with a crimping sleeve 56. The gas discharge hose 43 is slipped onto a connecting port of the adapter 49 and fastened pressure-tightly and gas-tightly thereon with a crimping sleeve 57.

Unlike in the first exemplary embodiment, in the third exemplary embodiment the gas infeed hose 42 and the gas discharge hose 43 are brought together upstream of the hollow body 41 and there form a twin hose 58 with two lines arranged next to one another which constitute part of the gas infeed hose 42 and the gas discharge hose 43. In this case, the gas discharge hose 43 is arranged next to the gas infeed hose 42 (as shown in FIGS. 10 to 12). The advantage is that only one connection is present, such that the passage is easier to close and the risk of microbes passing therethrough is reduced. The gas discharge hose 43 and the gas infeed hose 42 have a half moon-shaped or semicircular line cross-section in the region of the twin hose 58.

When in operation, the flushing fluid is fed into the medical placeholder through the adapter 48. The flushing fluid flows through the gas infeed hose 42 and opens the valve 44 when pressure is sufficient. The flushing fluid then flows through the inflow opening 50 into the hollow body 41 and through the hollow body 41. The flushing fluid flows through the gas discharge hose 43 to the initially closed valve 45. A pressure then builds up in the interior of the hollow body 41, by which the hollow body 41 is transferred into the expanded state. As soon as the pressure is sufficient at the valve 45 in the gas discharge hose 43, the valve 45 opens and the flushing fluid flows out through the gas discharge hose 43 and the adapter 49.

In the compressed state, the hollow body 41 may also be introduced into a cavity through a small opening. The hollow body 41 may be expanded therein and in this way the external shape of the hollow body 41 may be adapted to the cavity. The expanded hollow body 41, or the placeholder in the expanded state, thus mechanically supports and stabilizes the cavity. If the placeholder is no longer needed, the hollow body 41 is transferred back into the compressed state, for example by being evacuated. The hollow body 41 is then removed from the cavity through a narrow opening. If, in particular, the cavity is a cavity in a bone, this bone defect may in this way be carefully treated.

Oxygen is contained in the flushing fluid. The flushing fluid discharges oxygen through the wall of the hollow body 41 to the surroundings of the hollow body 41. At the same time, the flowing flushing fluid absorbs carbon dioxide, which diffuses through the wall of the hollow body 41 into the interior space, from the surroundings of the hollow body 41 and conveys the carbon dioxide away from the medical placeholder through the adapter 29. In this way, the surroundings of the hollow body 41 are supplied with oxygen and the absorption of carbon dioxide prevents over-acidification of the surroundings of the hollow body 41.

In the gas infeed hose 42 and/or in the gas discharge hose 43, it is also preferably possible to arrange sterile filters 19 which are impermeable to microbes but permeable to gases. Microbes which might otherwise reach the hollow body 41 and/or might be conveyed away from the hollow body 41 through the adapter 49 may be removed from the flushing fluid with the sterile filter 19. This reduces the risk of infection for the treated patient and the attending personnel.

The sterile filter 19 may preferably be arranged in the gas infeed hose 42 or the gas discharge hose 43 downstream of the valve 44 or the valve 45 in the direction of flow or the sterile filters 19 may be arranged in the gas infeed hose 42 and in the gas discharge hose 43 downstream of the valves 44, 45.

The hollow body 41 and/or the twin hose 58 are coated with an antiseptic substance or a soluble antiseptic substance is contained in the material of the hollow body 41, in order to prevent an infection.

To treat the surroundings of the hollow body 41, feedthroughs 18 are arranged in at least one wall of the hollow body 41 or of the at least one plastic material of the hollow body 41, the feedthroughs 18 having openings pointing in the direction of the outside of the hollow body 41, the openings connecting at least one duct (not shown) with the surroundings of the hollow body 41 in a manner permeable to liquids and gases. The at least one duct may be provided for feeding liquids into the hollow body 41 to the feedthroughs 18. In addition, the at least one duct may be connected with a feed hose (not shown) for pharmaceutical active ingredient solutions. In this way a pharmaceutical active ingredient solution can be delivered at the surface of the hollow body 41.

Figure 13:
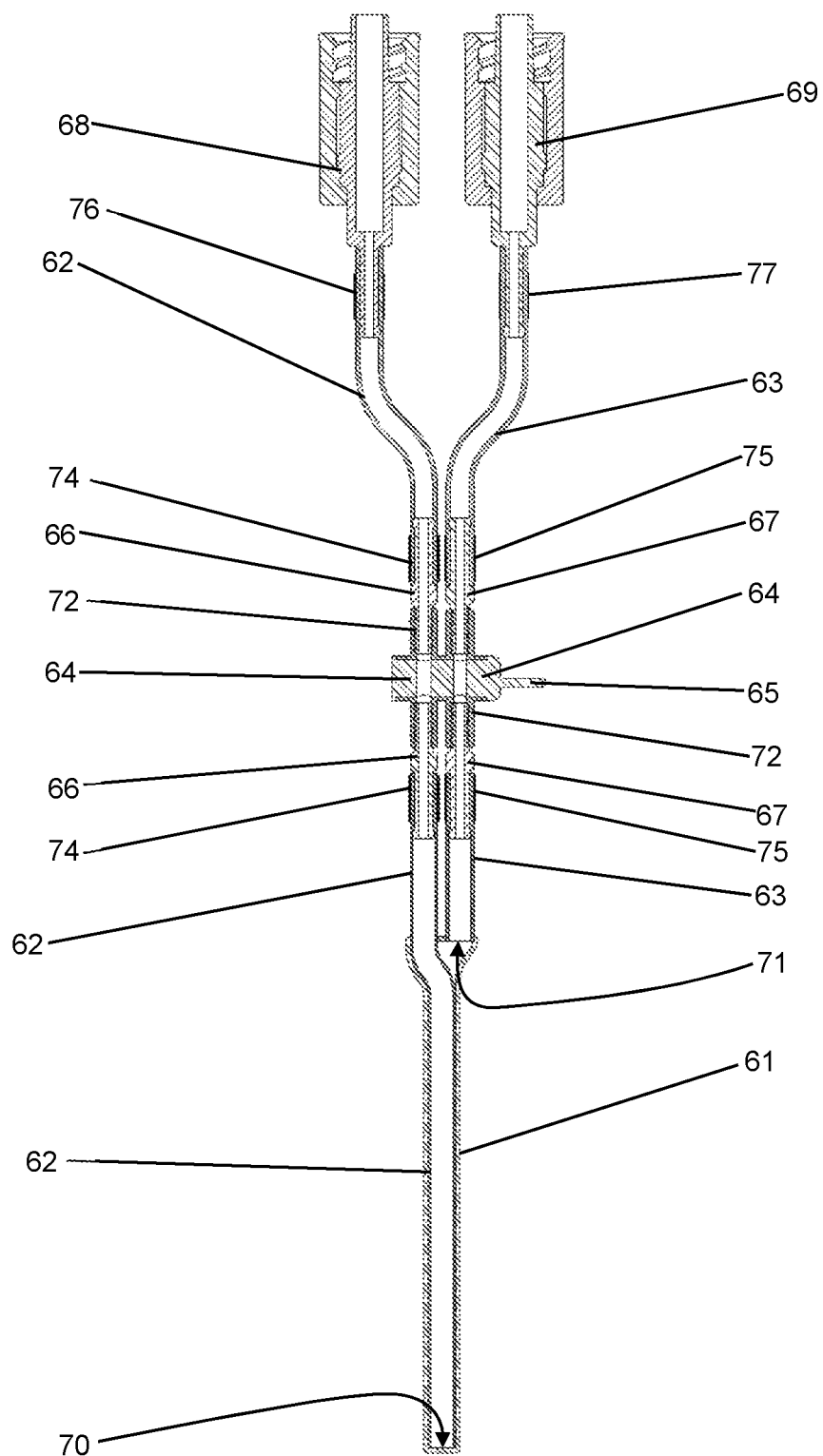
FIG. 13 is a schematic cross-sectional view of a fourth exemplary medical placeholder according to the invention in the compressed state.
Figure 14:
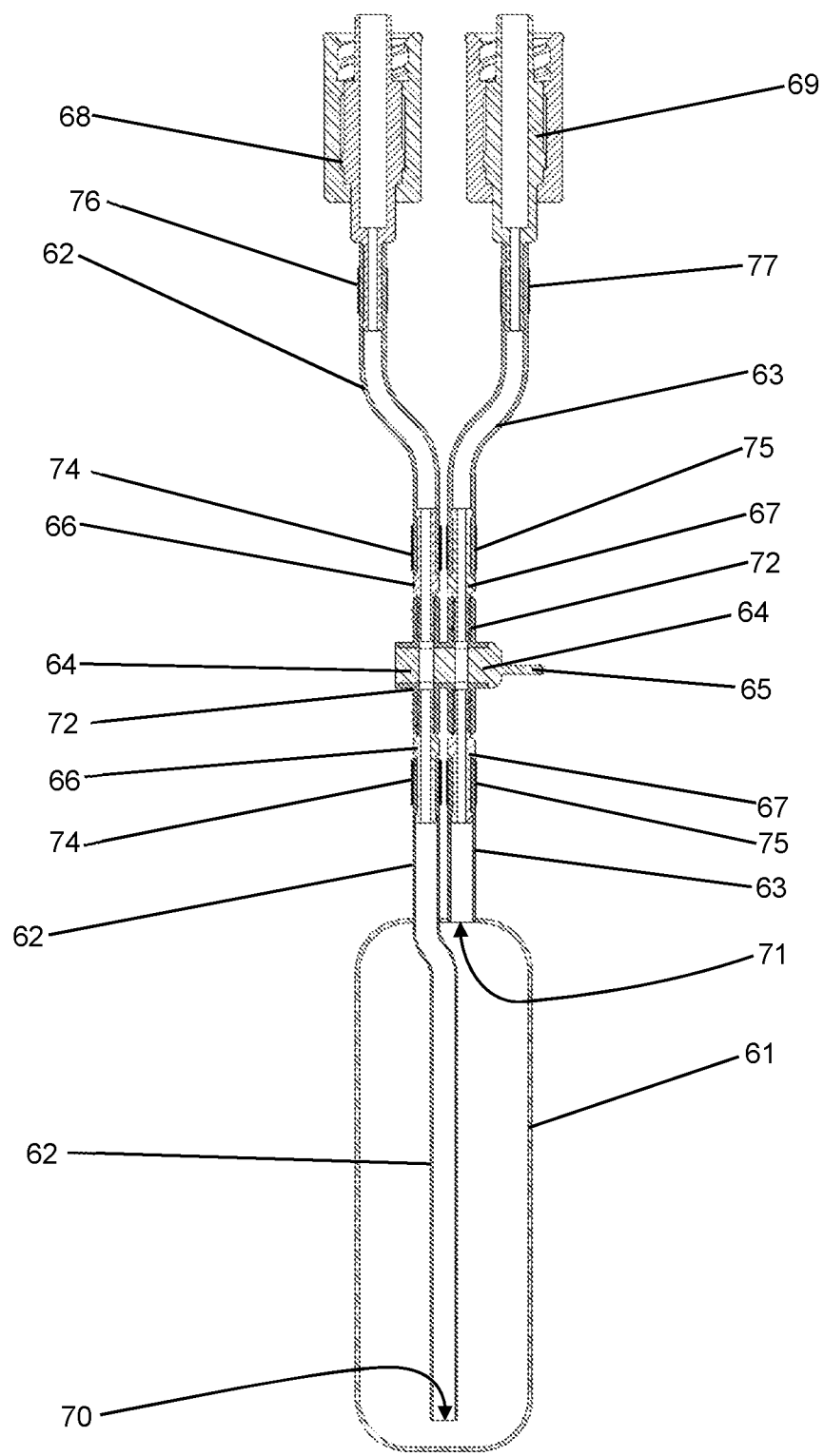
FIG. 14 is a schematic cross-sectional view of the fourth exemplary medical placeholder according to FIG. 13 in the expanded state.
Figure 15:
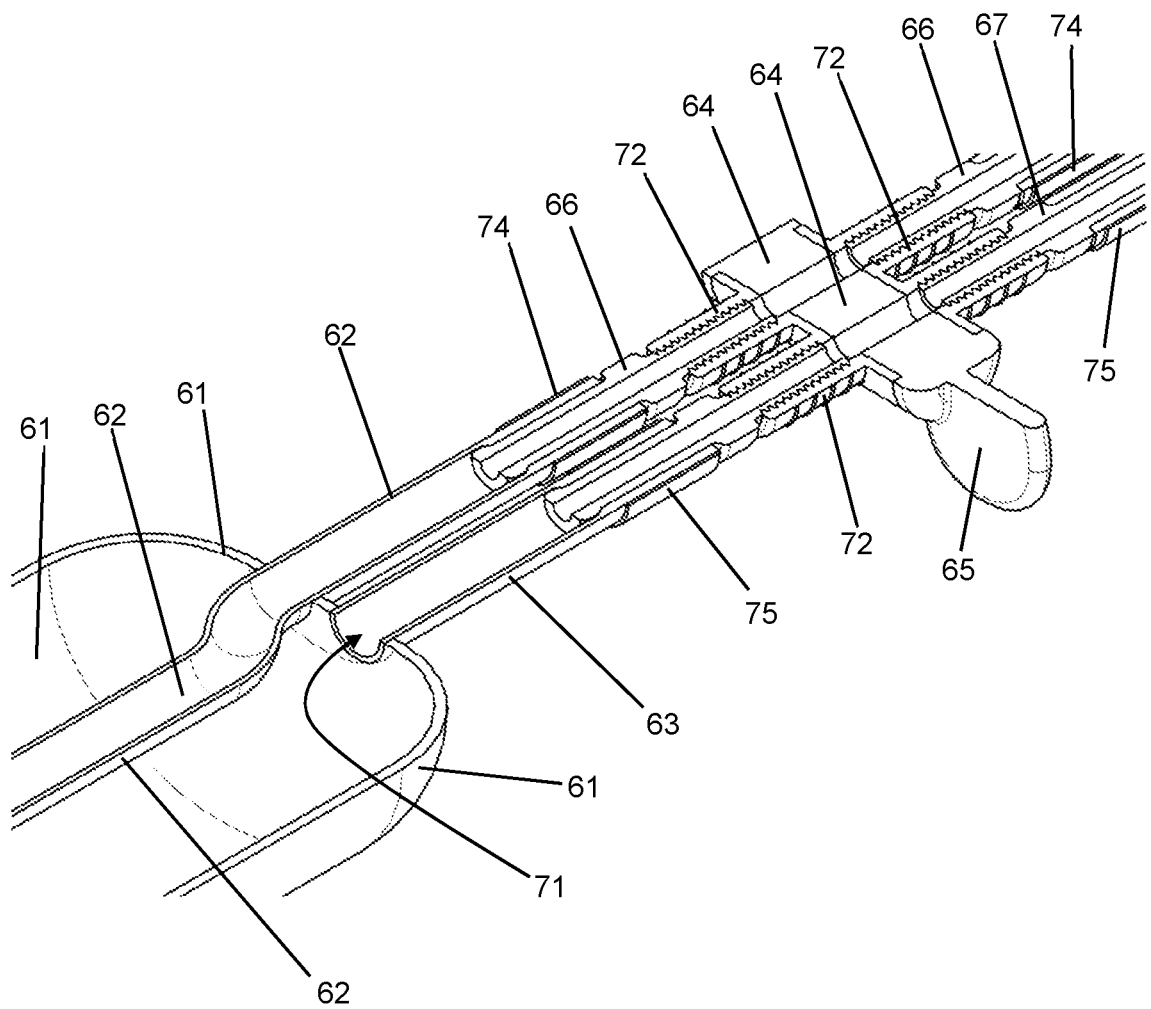
FIG. 15 shows a schematic perspective partial cross-sectional view of the fourth exemplary medical placeholder according to FIGS. 13 and 14 in the expanded state.

FIGS. 13 to 15 show illustrations of a fourth embodiment or example medical placeholder according to the invention. FIG. 13 shows the placeholder in the compressed state and FIGS. 14 and 15 show the placeholder in the expanded state.

The fourth medical placeholder according to the invention has a hollow body 61 of an elastically or plastically deformable plastic material. The hollow body 61 is expandable, in that it is inflated with a flushing gas or in that a flushing liquid is forced under pressure into the hollow body 61. The hollow body 61 for example consists of a rubber.

The material used for the hollow body 61 is permeable to gaseous molecular oxygen and to gaseous carbon dioxide. The hollow body 61 or the material from which the hollow body 61 is made to this end has a permeability coefficient for oxygen of greater than or equal to 0.5 $cm^3/(m^2*d*bar)$ and a permeability coefficient for carbon dioxide of greater than or equal to 0.5 $cm^3/(m^2*d*bar)$. The permeability coefficient is determined pursuant to DIN 53380-4 (11/2006).

For feeding in of a flushing fluid (a flushing gas or a flushing liquid), an interior space of the hollow body 61 is connected with a gas infeed hose 62 of plastic material. For discharge of the flushing fluid (the flushing gas or flushing liquid) from the hollow body 61, the interior space of the hollow body 61 is connected with a gas discharge hose 63 of plastic material. The gas infeed hose 62 and the gas discharge hose 63 are flexible and movable at least in places. A valve 64 in the form of a manually operable rotary valve is arranged in the gas infeed hose 62 and in the gas discharge hose 63, the rotary valve 64 being operable via a valve handle 65. The valve 64 may be used for manual closure and opening of the gas infeed hose 62 and the gas discharge hose 63. The gas infeed hose 62 and the gas discharge hose 63 may also be capable of individual, mutually independent manual closure and opening. A dynamic pressure determined by the cross-section of the gas discharge hose 63 in this case is selected such that the pressure of the flushing fluid is sufficient to transfer the hollow body 61 from the compressed state (see FIG. 13) into the expanded state when the valve 64 is open (see FIGS. 14 and 15).

The valve 64 is connected via connecting sleeves 66, 67 to the gas infeed hose 62 and the gas discharge hose 63. To this end, the gas infeed hose 62 is slipped onto the connecting sleeve 66 and fastened there with a crimping sleeve 74. The gas discharge hose 63 is likewise slipped onto the connecting sleeve 67 and fastened there with a crimping sleeve 75.

The gas infeed hose 62 ends at its rear in an adapter 68 in the form of a Luer Lock adapter. The gas discharge hose 63 likewise ends at its rear in an adapter 69 in the form of a Luer Lock adapter. The flushing fluid is fed in and discharged through the adapters 68, 69.

The gas infeed hose 62 leads via an inflow opening 70 into the front part of the interior of the hollow body 61, while the gas discharge hose 63 is connected with the interior space of the hollow body 61 via an outflow opening 71 at the opposing rear of the interior space of the hollow body 61. In this way, it is ensured that the flushing fluid can flow along the surface of the wall of the entire hollow body 61 and gas exchange of oxygen and carbon dioxide can thereby take place through the wall over the entire length of the hollow body 61.

The valve 64 has a valve housing 72. The valve housing 72 is connected via an internal thread to external threads of the connecting sleeve 66 and of the connecting sleeve 67. All the connections are gas-tight and pressure-tight.

The gas infeed hose 62 is slipped onto a connecting port of the adapter 68 and fastened pressure-tightly and gas-tightly thereon with a crimping sleeve 76. The gas discharge hose 63 is slipped onto a connecting port of the adapter 69 and fastened pressure-tightly and gas-tightly thereon with a crimping sleeve 77.

When in operation, the flushing fluid is fed into the medical placeholder through the adapter 68. When the valve 64 is open, the flushing fluid flows through the gas infeed hose 62. The flushing fluid then flows through the inflow opening 70 into the hollow body 61 and through the hollow body 61. A pressure then builds up in the interior of the hollow body 61, by which the hollow body 61 is transferred into the expanded state.

In the compressed state, with the valve 64 closed, the hollow body 61 may also be introduced into a cavity through a small opening. The hollow body 61 may be expanded therein and in this way the external shape of the hollow body 61 may be adapted to the cavity. The expanded hollow body 61, or the placeholder in the expanded state, thus mechanically supports and stabilizes the cavity. If the placeholder is no longer needed, the hollow body 61 is transferred back into the compressed state, for example by being evacuated. The hollow body 61 is then removed from the cavity through a narrow opening. If, in particular, the cavity is a cavity in a bone, this bone defect may in this way be carefully treated.

Oxygen is contained in the flushing fluid. The flushing fluid discharges oxygen through the wall of the hollow body 61 to the surroundings of the hollow body 61. At the same time, the flowing flushing fluid absorbs carbon dioxide, which diffuses through the wall of the hollow body 61 into the interior space, from the surroundings of the hollow body 61 and conveys the carbon dioxide away from the medical placeholder through the adapter 69. In this way, the surroundings of the hollow body 61 are supplied with oxygen and the absorption of carbon dioxide prevents over-acidification of the surroundings of the hollow body 61.

In the gas infeed hose 62 and/or in the gas discharge hose 63, it is also preferably possible to arrange sterile filters 19 which are impermeable to microbes but permeable to gases. Microbes which might otherwise reach the hollow body 61 and/or might be conveyed away from the hollow body 61 through the adapter 69 may be removed from the flushing fluid with the sterile filter 19. This reduces the risk of infection for the treated patient and the attending personnel.

The sterile filter 19 may preferably be arranged in the gas infeed hose 62 or the gas discharge hose 63 downstream of the valve 64 in the direction of flow or the sterile filters 19 may be arranged in the gas infeed hose 62 and in the gas discharge hose 63 downstream of the valves 64.

The hollow body 61 and/or the hoses 62, 63 are coated in the region of the hollow body 61 with an antiseptic substance or a soluble antiseptic substance is contained in the material of the hollow body 61, in order to prevent an infection.

To treat the surroundings of the hollow body 61, feedthroughs 18 are arranged in at least one wall of the hollow body 61 or of the at least one plastic material of the hollow body 61, the feedthroughs 18 having openings pointing in the direction of the outside of the hollow body 61, the openings connecting at least one duct (not shown) with the surroundings of the hollow body 61 in a manner permeable to liquids and gases. The at least one duct may be provided for feeding liquids into the hollow body 61 to the feedthroughs 18. In addition, the at least one duct may be connected with a feed hose (not shown) for pharmaceutical active ingredient solutions. In this way a pharmaceutical active ingredient solution can be delivered at the surface of the hollow body 61.

Figure 16:
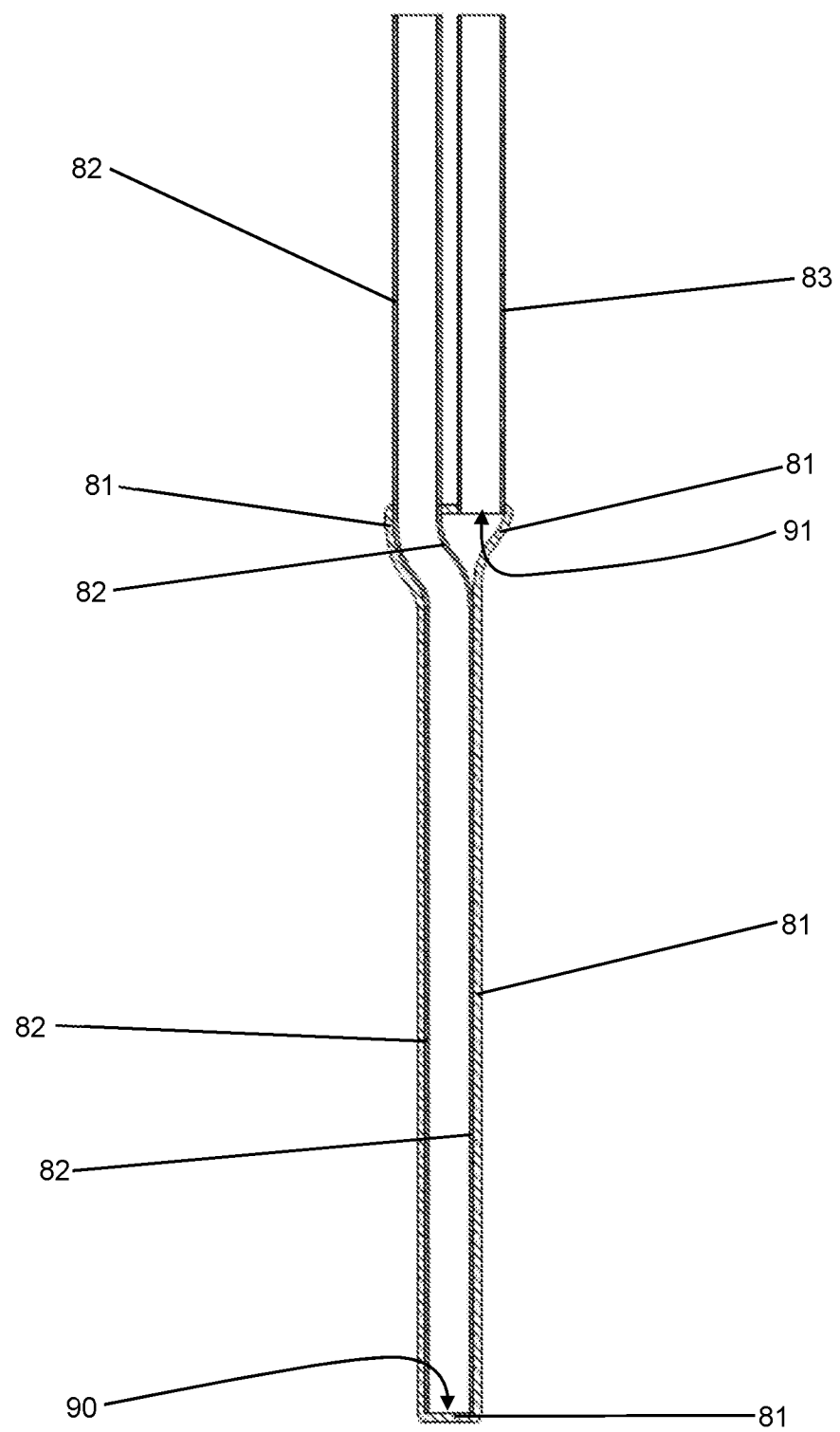
FIG. 16 is a schematic cross-sectional view of a fifth exemplary medical placeholder according to the invention in the compressed state.
Figure 17:
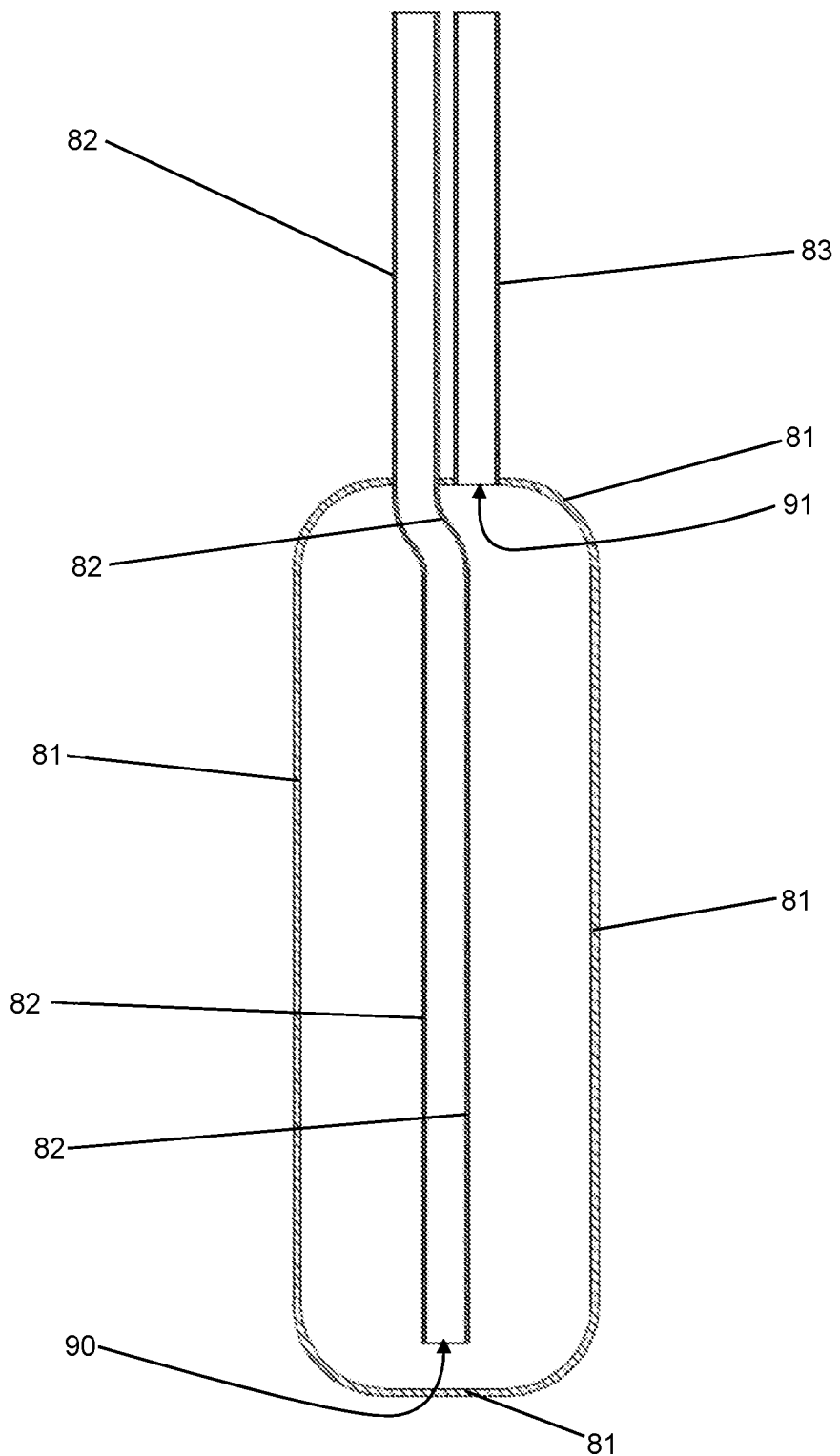
FIG. 17 is a schematic cross-sectional view of the fifth exemplary medical placeholder according to FIG. 16 in the expanded state.

FIGS. 16 and 17 are illustrations of a fifth embodiment or example of a medical placeholder according to the invention of very simple structure. FIG. 16 shows the placeholder in the compressed state and FIG. 17 shows the placeholder in the expanded state.

The fifth medical placeholder according to the invention has a hollow body 81 of an elastically or plastically deformable plastic material. The hollow body 81 is expandable, in that it is inflated with a flushing gas or in that a flushing liquid is forced under pressure into the hollow body 81. The hollow body 81 for example consists of a rubber.

The material used for the hollow body 81 is permeable to gaseous molecular oxygen and to gaseous carbon dioxide. The hollow body 81 or the material from which the hollow body 81 is made to this end has a permeability coefficient for oxygen of greater than or equal to 0.5 $cm^3/(m^2*d*bar)$ and a permeability coefficient for carbon dioxide of greater than or equal to 0.5 $cm^3/(m^2*d*bar)$. The permeability coefficient is determined pursuant to DIN 53380-4 (11/2006).

For feeding in of a flushing fluid (a flushing gas or a flushing liquid), an interior space of the hollow body 81 is connected with a gas infeed hose 82 of plastic material. For discharge of the flushing fluid (the flushing gas or flushing liquid) from the hollow body 81, the interior space of the hollow body 81 is connected with a gas discharge hose 83 of plastic material. The gas infeed hose 82 and the gas discharge hose 83 are flexible and movable at least in places. A dynamic pressure determined by the cross-section of the gas discharge hose 83 in this case is selected such that the pressure of the flushing fluid is sufficient to transfer the hollow body 81 from the compressed state (see FIG. 16) into the expanded state (see FIG. 17).

The gas infeed hose 82 leads via an inflow opening 90 into the front part of the interior of the hollow body 81, while the gas discharge hose 83 is connected with the interior space of the hollow body 81 via an outflow opening 91 at the opposing rear of the interior space of the hollow body 81. In this way, it is ensured that the flushing fluid can flow along the surface of the wall of the entire hollow body 81 and gas exchange of oxygen and carbon dioxide can thereby take place through the wall over the entire length of the hollow body 81.

When in operation, the flushing fluid is fed into the medical placeholder through the gas infeed hose 82. The flushing fluid flows through the inflow opening 90 into the hollow body 81 and through the hollow body 81. A pressure then builds up in the interior of the hollow body 81, by which the hollow body 81 is transferred into the expanded state.

In the compressed state, the hollow body 81 may also be introduced into a cavity through a small opening. The hollow body 81 may be expanded therein and in this way the external shape of the hollow body 81 may be adapted to the cavity. The expanded hollow body 81, or the placeholder in the expanded state, thus mechanically supports and stabilizes the cavity. If the placeholder is no longer needed, the hollow body 81 is transferred back into the compressed state, for example by being evacuated. The hollow body 81 is then removed from the cavity through a narrow opening. If, in particular, the cavity is a cavity in a bone, this bone defect may in this way be carefully treated.

Oxygen is contained in the flushing fluid. The flushing fluid discharges oxygen through the wall of the hollow body 81 to the surroundings of the hollow body 81. At the same time, the flowing flushing fluid absorbs carbon dioxide, which diffuses through the wall of the hollow body 81 into the interior space, from the surroundings of the hollow body 81 and conveys the carbon dioxide away from the medical placeholder through the gas discharge hose 83. In this way, the surroundings of the hollow body 81 are supplied with oxygen and the absorption of carbon dioxide prevents over-acidification of the surroundings of the hollow body 81.

In the gas infeed hose 82 and/or in the gas discharge hose 83, it is also preferably possible to arrange sterile filters 19 which are impermeable to microbes but permeable to gases. Microbes which might otherwise reach the hollow body 81 and/or might be conveyed away from the hollow body 81 through the gas discharge hose 83 may be removed from the flushing fluid with the sterile filter 19. This reduces the risk of infection for the treated patient and the attending personnel.

The hollow body 81 and/or the hoses 82, 83 are coated in the region of the hollow body 81 with an antiseptic substance or a soluble antiseptic substance is contained in the material of the hollow body 81, in order to prevent an infection.

To treat the surroundings of the hollow body 81, feed-throughs 18 are arranged in at least one wall of the hollow body 81 or of the at least one plastic material of the hollow body 81, the feedthroughs 18 having openings pointing in the direction of the outside of the hollow body 81, the openings connecting at least one duct (not shown) with the surroundings of the hollow body 81 in a manner permeable to liquids and gases. The at least one duct may be provided for feeding liquids into the hollow body 81 to the feedthroughs 18. In addition, the at least one duct may be connected with a feed hose (not shown) for pharmaceutical active ingredient solutions. In this way a pharmaceutical active ingredient solution can be delivered at the surface of the hollow body 81.

Figure 18:
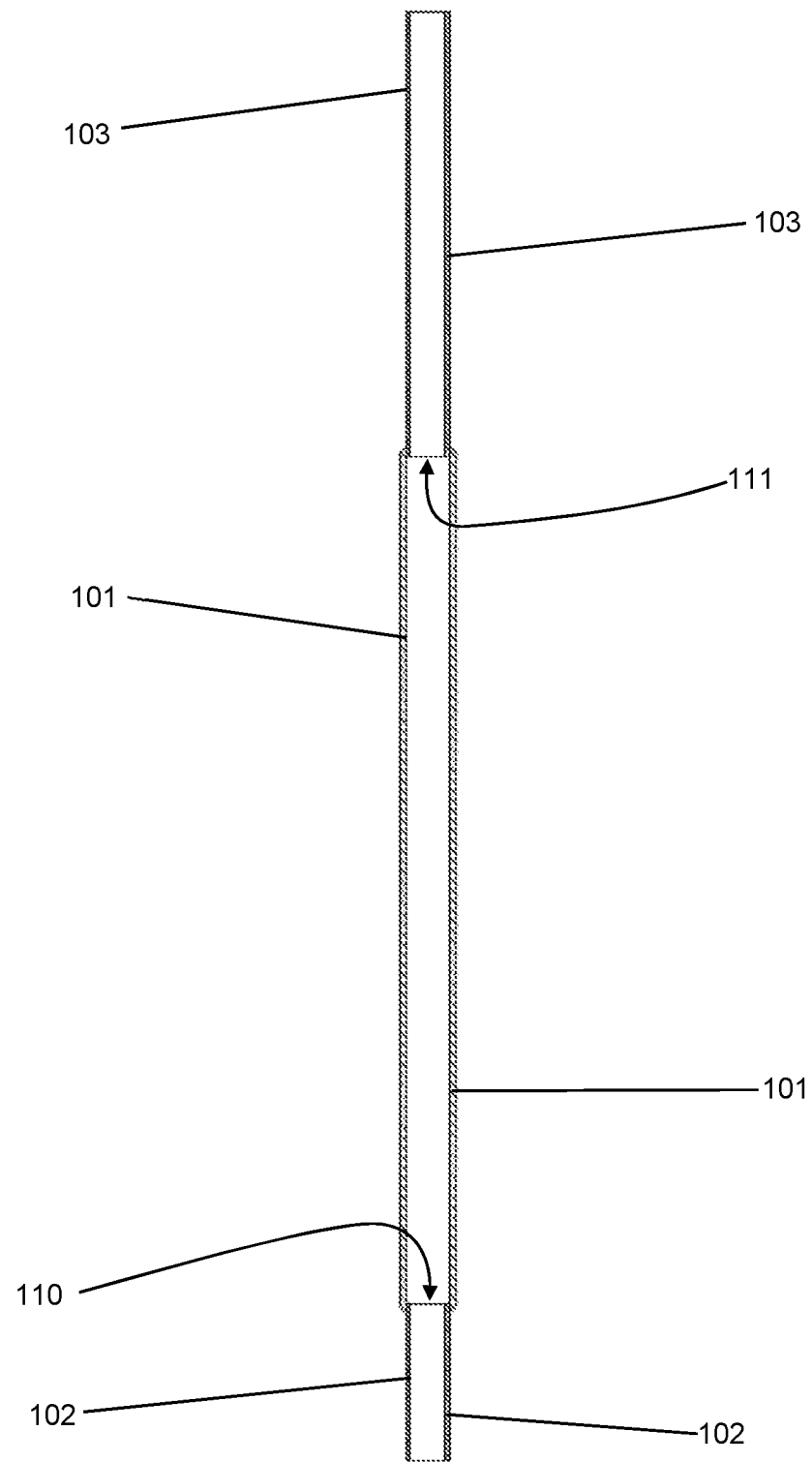
FIG. 18 is a schematic cross-sectional view of a sixth exemplary medical placeholder according to the invention in the compressed state.
Figure 19:
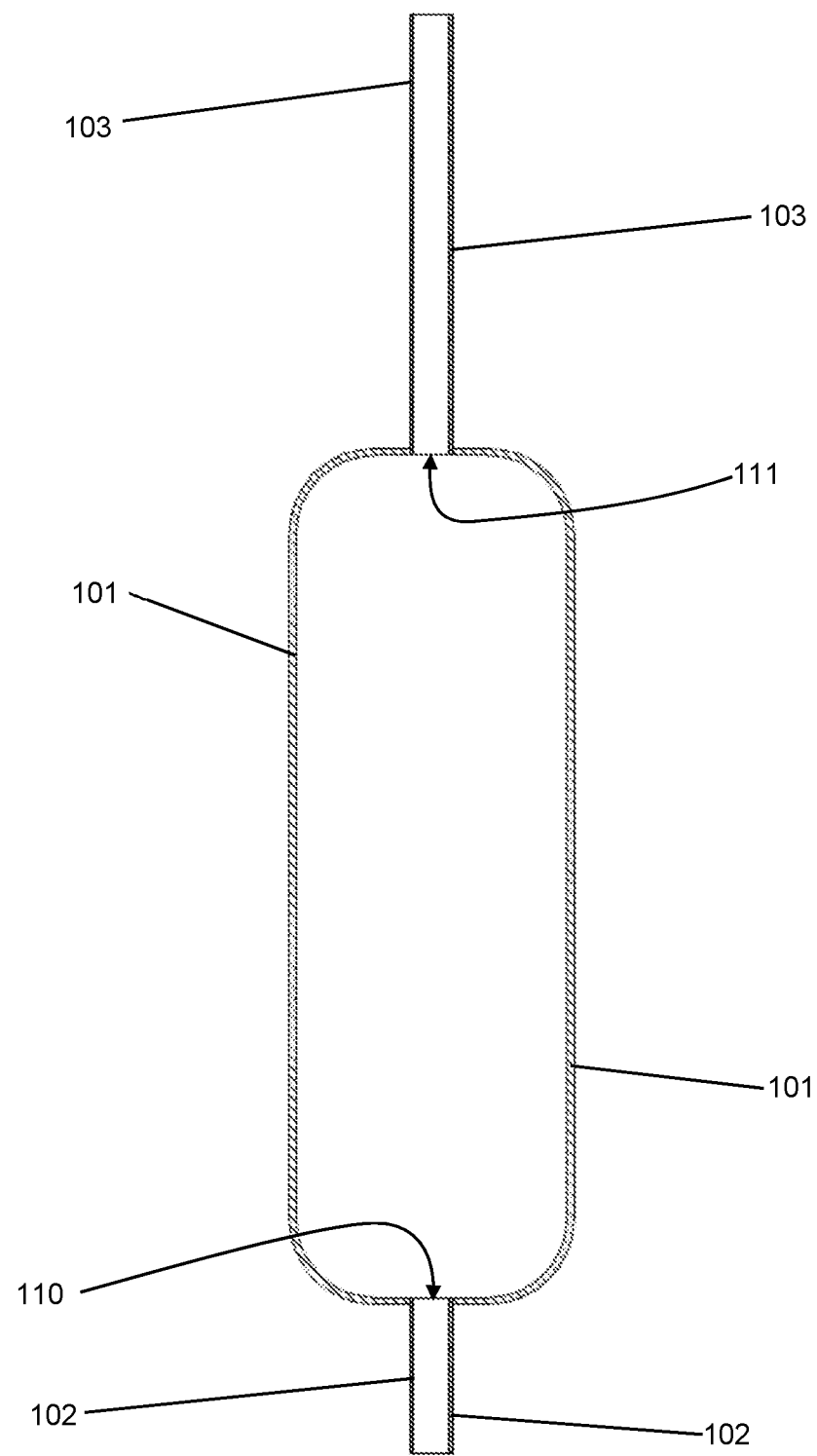
FIG. 19 is a schematic cross-sectional view of the sixth exemplary medical placeholder according to FIG. 18 in the expanded state.

FIGS. 18 and 19 are illustrations of a sixth embodiment or example of a medical placeholder according to the invention of very simple structure. FIG. 18 shows the placeholder in the compressed state and FIG. 19 shows the placeholder in the expanded state.

The sixth medical placeholder according to the invention has a hollow body 101 of an elastically or plastically deformable plastic material. The hollow body 101 is expandable, in that it is inflated with a flushing gas or in that a flushing liquid is forced under pressure into the hollow body 101. The hollow body 81 example consists of a rubber.

The material used for the hollow body 101 is permeable to gaseous molecular oxygen and to gaseous carbon dioxide. The hollow body 101 or the material from which the hollow body 101 is made to this end has a permeability coefficient for oxygen of greater than or equal to 0.5 $cm^3/(m^2*d*bar)$ and a permeability coefficient for carbon dioxide of greater than or equal to 0.5 $cm^3/(m^2*d*bar)$. The permeability coefficient is determined pursuant to DIN 53380-4 (11/2006).

For feeding in of a flushing fluid (a flushing gas or a flushing liquid), an interior space of the hollow body 101 is connected with a gas infeed hose 102 of plastic material. For discharge of the flushing fluid (the flushing gas or flushing liquid) from the hollow body 101, the interior space of the hollow body 101 is connected with a gas discharge hose 103 of plastic material. The gas infeed hose 102 and the gas discharge hose 103 are flexible and movable at least in places. A dynamic pressure determined by the cross-section of the gas discharge hose 103 in this case is selected such that the pressure of the flushing fluid is sufficient to transfer the hollow body 101 from the compressed state (see FIG. 18) into the expanded state (see FIG. 19).

The gas infeed hose 102 leads via an inflow opening 110 into the front part of the interior of the hollow body 101, while the gas discharge hose 103 is connected with the interior space of the hollow body 101 via an outflow opening 111 at the opposing rear of the interior space of the hollow body 101. In this way, it is ensured that the flushing fluid can flow along the surface of the wall of the entire hollow body 101 and gas exchange of oxygen and carbon dioxide can thereby take place through the wall over the entire length of the hollow body 101.

When in operation, the flushing fluid is fed into the medical placeholder through the gas infeed hose 102. The flushing fluid flows through the inflow opening 110 into the hollow body 101 and through the hollow body 101. A pressure then builds up in the interior of the hollow body 101, by which the hollow body 101 is transferred into the expanded state.

In the compressed state, the hollow body 101 may also be introduced into a cavity through a small opening. The hollow body 101 may be expanded therein and in this way the external shape of the hollow body 101 may be adapted to the cavity. The expanded hollow body 101, or the placeholder in the expanded state, thus mechanically supports and stabilizes the cavity. If the placeholder is no longer needed, the hollow body 101 is transferred back into the compressed state, for example by being evacuated. The hollow body 101 is then removed from the cavity through a narrow opening. If, in particular, the cavity is a cavity in a bone, this bone defect may in this way be carefully treated.

Oxygen is contained in the flushing fluid. The flushing fluid discharges oxygen through the wall of the hollow body 101 to the surroundings of the hollow body 101. At the same time, the flowing flushing fluid absorbs carbon dioxide, which diffuses through the wall of the hollow body 101 into the interior space, from the surroundings of the hollow body 101 and conveys the carbon dioxide away from the medical placeholder through the gas discharge hose 103. In this way, the surroundings of the hollow body 101 are supplied with oxygen and the absorption of carbon dioxide prevents over-acidification of the surroundings of the hollow body 101.

In the gas infeed hose 102 and/or in the gas discharge hose 103, it is also preferably possible to arrange sterile filters 19 which are impermeable to microbes but permeable to gases. Microbes which might otherwise reach the hollow body 101 and/or might be conveyed away from the hollow body 101 through the gas discharge hose 103 may be removed from the flushing fluid with the sterile filter 19. This reduces the risk of infection for the treated patient and the attending personnel.

The hollow body 101 and/or the hoses 102, 103 are coated in the region of the hollow body 101 with an antiseptic substance or a soluble antiseptic substance is contained in the material of the hollow body 101, in order to prevent an infection.

To treat the surroundings of the hollow body 101, feedthroughs 18 are arranged in at least one wall of the hollow body 101 or of the at least one plastic material of the hollow body 101, the feedthroughs 18 having openings pointing in the direction of the outside of the hollow body 101, the openings connecting at least one duct (not shown) with the surroundings of the hollow body 101 in a manner permeable to liquids and gases. The at least one duct may be provided for feeding liquids into the hollow body 101 to the feedthroughs 18. In addition, the at least one duct may be connected with a feed hose (not shown) for pharmaceutical active ingredient solutions. In this way a pharmaceutical active ingredient solution can be delivered at the surface of the hollow body 101.

The features of the invention disclosed in the above description, as well as in the claims, figures and exemplary embodiments, may be essential both individually and in any desired combination to realization of the invention in its various embodiments. Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the disclosure.

The invention claimed is:

1. A medical placeholder comprising:
    a hollow body which is expandable, defines an interior space in the interior of the hollow body, and a part of the hollow body or the hollow body fully consists of at least one plastic material that is permeable to oxygen and carbon dioxide;
    a gas infeed hose which is connected or connectable in a gas-permeable manner with the interior space of the hollow body;
    a gas discharge hose which is connected or connectable in a gas-permeable manner with the interior space of the hollow body;
    a one-way valve arranged in the gas infeed hose; and a pressure relief valve arranged in the gas discharge hose;
    wherein the hollow body or the at least one plastic material of the hollow body has a permeability coefficient for oxygen of greater than or equal to 0.5 cm$^3$/(m$^2$*d*bar) and a permeability coefficient for carbon dioxide of greater than or equal to 0.5 cm$^3$/(m$^2$*d*bar).

2. The medical placeholder according to claim 1, wherein the gas infeed hose has an inflow opening that opens into the interior space, the gas discharge hose has an outflow opening that forms a point where the interior space opens into the gas discharge hose, and the inflow opening of the gas infeed hose is arranged spatially separately from the outflow opening of the gas discharge hose.

3. The medical placeholder according to claim 2, wherein the hollow body has a first end and an opposite second end and the inflow opening of the gas infeed hose is arranged at the first end of the hollow body and the outflow opening of the gas discharge hose is arranged at the second end of the hollow body opposite the first end.

4. The medical placeholder according to claim 1, wherein the gas infeed hose and the gas discharge hose are arranged at least in part coaxially to one another.

5. The medical placeholder according to claim 1, wherein the gas infeed hose and the gas discharge hose are connected to one another.

6. The medical placeholder according to claim 1, further comprising a common outer hose subdivided by a partition which defines the gas infeed hose on one side and the gas discharge hose on the other side.

7. The medical placeholder according to claim 1, further comprising a sterile filter which is impermeable to microbes but permeable to gases arranged in the gas infeed hose and/or the gas discharge hose.

8. The medical placeholder according to claim 1, further comprising a third valve arranged in the gas infeed hose and/or the gas discharge hose configured to shut off the gas infeed hose and/or the gas discharge hose.

9. The medical placeholder according to claim 7, wherein the sterile filter is arranged in the gas infeed hose and/or the gas discharge hose downstream of the one-way valve and/or the pressure relief valve in the direction of flow.

10. The medical placeholder according to claim 1, wherein the pressure relief valve has an adjustable opening pressure.

11. The medical placeholder according to claim 1, wherein the gas infeed hose and the gas discharge hose consist of a material which is not permeable to oxygen and carbon dioxide.

12. The medical placeholder according to claim 1, wherein the hollow body or the at least one plastic material of the hollow body contains at least one antiseptic active ingredient or is coated with at least one antiseptic active ingredient.

13. The medical placeholder according to claim 1, wherein the hollow body or the at least one plastic material of the hollow body defines at least one wall and the medical placeholder further comprises:
    a feed hose configured to receive pharmaceutical active ingredient solutions;
    a connection adapter arranged at the feed hose;
    at least one duct connected with the feed hose; and
    feedthroughs arranged in the at least one wall of the hollow body or of the at least one plastic material of the hollow body, the feedthroughs having openings pointing in the direction of the outside of the hollow body and connecting the at least one duct with the surroundings of the hollow body in a manner permeable to liquids and gases, wherein the at least one duct is configured to feed liquids into the hollow body via the feedthroughs.

14. The medical placeholder according to claim 1, wherein the hollow body rests in an uninflated state against the gas infeed hose and/or against the gas discharge hose and wherein the hollow body or the at least one plastic material is inflatable in the manner of a balloon.

15. A method for gas-flushing a surface of a medical placeholder comprising the following steps:
    A) providing a medical placeholder according to claim 1 as an initial step;
    B) expanding the hollow body by feeding a flushing liquid containing oxygen or a flushing gas containing oxygen into the interior space of the hollow body, thereby enlarging the interior space of the hollow body;
    C) delivering gaseous oxygen from the flushing liquid or the flushing gas through the at least one plastic material defining the interior space to the surroundings of the hollow body;
    D) absorbing gaseous carbon dioxide from the surroundings of the hollow body through the at least one plastic material defining the interior space into the flushing liquid or the flushing gas;
    E) passing the flushing liquid or the flushing gas through the interior space of the hollow body; and F) discharging the flushing liquid or flushing gas out of the interior space.

16. The method according to claim 15, wherein the method is not performed for medical treatment of a human or animal body.

17. The method according to claim 15, further comprising a step of introducing the hollow body into a cavity prior to step B), wherein during step B), the shape of the expanded hollow body adapts at least in places to the shape of the cavity and during steps C) and D) rests at least in places against the cavity.

18. The method according to claim 15, wherein the hollow body is expanded in step B) until a minimum pressure is reached, wherein the pressure relief valve opens once the minimum pressure is reached, the flushing liquid or the flushing gas being discharged through this pressure relief valve out of the interior space of the hollow body during step F).

* * * * *